(12) United States Patent
van der Stelt et al.

(10) Patent No.: US 7,960,560 B2
(45) Date of Patent: Jun. 14, 2011

(54) 1-(BIPHENYL-4-YLMETHYL)IMIDAZOLI-DINE-2,4-DIONE

(75) Inventors: Marcelis van der Stelt, Oss (NL);
Joseph Maria Gerardus Barbara Cals, Oss (NL)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 12/628,523

(22) Filed: Dec. 1, 2009

(65) Prior Publication Data
US 2010/0144723 A1 Jun. 10, 2010

Related U.S. Application Data

(60) Provisional application No. 61/119,188, filed on Dec. 2, 2008.

(30) Foreign Application Priority Data

Dec. 2, 2008 (EP) .................................. 08170483

(51) Int. Cl.
| | |
|---|---|
| C07D 487/10 | (2006.01) |
| C07D 233/40 | (2006.01) |
| C07D 401/10 | (2006.01) |
| C07D 417/10 | (2006.01) |
| C07D 413/10 | (2006.01) |
| A61K 31/54 | (2006.01) |
| A61K 31/5377 | (2006.01) |
| A61K 31/4523 | (2006.01) |
| A61K 31/4166 | (2006.01) |

(52) U.S. Cl. ............... 548/301.4; 548/318.5; 548/319.5; 548/320.5; 546/210; 544/60; 544/139; 514/277.8; 514/235.8; 514/326; 514/389

(58) Field of Classification Search .................. None
See application file for complete search history.

(56) References Cited

FOREIGN PATENT DOCUMENTS
| | | |
|---|---|---|
| WO | WO 01/56996 | 8/2001 |
| WO | WO 2004/018433 | 3/2004 |
| WO | WO 2007/070760 | 6/2007 |

OTHER PUBLICATIONS

International Search Report for PCT/EP2009/066156 filed Jan. 12, 2009 mailed on Jan. 19, 2010; 4 pages.
Written Opinion for PCT/EP2009/066156 filed Jan. 12, 2009 mailed on Jan. 19, 2010; 5 pages.
Govaerts Sophie, J. et. al.; "Characterization of the pharmacology of imidazolidinedione derivatives at cannabinoid CB1 and CB2 receptors", European Journal of Pharmacology; vol. 495, No. 1; Jul. 8, 2004; pp. 43-53.
International Search Report for PCT/EP2009/066030 filed Nov. 30, 2009 mailed on May 2, 2010; 4 pages.

Primary Examiner — Kamal A Saeed
Assistant Examiner — Nyeemah Grazier
(74) Attorney, Agent, or Firm — Susan L. Hess

(57) ABSTRACT

The invention relates to A 1-(biphenyl-4-ylmethyl)imidazolidine-2,4-dione derivative having the general Formula I wherein $R_1$ is H, $(C_{1-6})$alkyl (optionally substituted with oxo, $OR_4$, $COOR_5$, halogen or CN), $(C_{2-6})$alkenyl, $(C_{2-6})$alkynyl, $(C_{3-6})$cycloalkyl or $(C_{3-6})$cycloalkyl$(C_{1-3})$alkyl; $R_2$ and $R_2'$ are independently H or $(C_{1-3})$alkyl; or $R_2$ and $R_2'$ form together with the carbon atom to which they are bound a $(C_{3-5})$cycloalkyl group; $R_3$ represents H or 1 to 4 F substituents; Y represents or $NR_8R_9$; X represents $CHR_6$, $CF_2$, O, S, SO or $SO_2$; $R_4$ and $R_5$ are $(C_{1-6})$alkyl; $R_6$ is H, $OR_7$ or CN; $R_7$ is $(C_{1-3})$alkyl; $R_8$ is $(C_{5-7})$cycloalkyl comprising a heteroatom selected from O, S, SO and $SO_2$; $R_9$ is H or $(C_{1-4})$alkyl; o and m represent the ortho or meta position of the substituent $Y-CH_2$; or a pharmaceutically acceptable salt thereof; as well as to the use of said 1-(biphenyl-4-ylmethyl)imidazolidine-2,4-dione derivatives in the treatment of pain such as for example perioperative pain, chronic pain, neuropathic pain, cancer pain and pain and spasticity associated with multiple sclerosis.

13 Claims, 1 Drawing Sheet

1-(BIPHENYL-4-YLMETHYL)IMIDAZOLIDINE-2,4-DIONE

This application is a non-provisional application that claims priority under 35 U.S.C. §119(e) of provisional application U.S. Ser. No. 61/119,188 filed Dec. 2, 2008, the contents of which are hereby incorporated by reference in its entirety.

BACKGROUND

The present invention relates to 1-(biphenyl-4-ylmethyl) imidazolidine-2,4-dione derivatives, to pharmaceutical compositions comprising the same and to the use of these 1-(biphenyl-4-ylmethyl)imidazolidine-2,4-dione derivatives in therapy, especially in the treatment of pain.

Pain is an unpleasant sensory and emotional experience associated with actual or potential tissue damage. Pain can be nociceptive or neuropathic in origin. Pain experienced as a consequence of arthritis is generally nociceptive in nature, caused by inflammation of tissue and stimulation of nociceptors. Major indications driving prevalence of nociceptive pains are low back pain, osteoarthritis, post-operative pain, and cancer-related pain. Major unmet needs for nociceptive pain are for improved efficacy and fewer side effects. The chronic pain market is currently dominated by non-steroidal anti-inflammatory drugs (NSAIDs) and cyclo-oxygenase COX-2 inhibitors. NSAIDs provide adequate analgesia to relieve mild to moderate pain and usually have greater effectiveness in inflammatory pain. Individual NSAIDs vary in their efficacy, and these variations are partly determined by differing COX-1/COX-2 selectivities. Consequently, patients may require to be treated with several different drugs before their pain is adequately treated. Side effects associated with drug therapy are an important factor in treatment choice, especially as many pain syndromes are long-term chronic conditions.

The most common side effects of NSAIDs are constipation and indigestion; most anti-inflammatory drugs are acidic in nature and promote acid production in the stomach. Other, serious side effects are gastrointestinal complications such as gastric ulcers, mucosal damage and peptic erosion. NSAIDs are thought to account for as many as 107,000 hospitalizations and 16,500 deaths due to ulcer complications in the US each year (Singh, *Recent considerations in nonsteroidal anti-inflammatory drug gastropathy*. Am. J. Med., 1998, 105: 31S-38S). Whilst COX-2 inhibitors have an improved gastrointestinal side effect profile, their use has been associated with increased risk of myocardial infarction and stroke and increased risk of hypertension.

Neuropathic pain, defined as chronic pain caused by injury, disease or dysfunction of the nervous system, is present in ~1% of the population; the largest patient populations include those with painful diabetic peripheral neuropathy, and those with neuralgia that persists after an attack of herpes zoster (post-herpetic neuralgia). It is characterized by a complex combination of symptoms, including spontaneous pain that can occur in the absence of tissue damage. Patients suffering from neuropathic pain also have increased sensitivity both to stimuli normally perceived as painful (hyperalgesia), as well as to stimuli that do not normally provoke pain (allodynia). These symptoms are often refractory to conventional analgesic therapies, with most patients achieving incomplete relief of their symptoms. Currently, antidepressants, anticonvulsants and opioids remain first-line treatment, with gabapentin as the gold standard. All of these drugs have significant side-effects that are dose limiting. In addition, efficacy is a considerable problem in the neuropathic pain market with current treatments showing a maximum of 50% reduction in overall pain scores from baseline. Consequently, there remains an unmet medical need for agents that have higher efficacy/responder rate, and with reduced side-effects compared with currently used drugs.

Emerging clinical evidence, as well as anecdotal reports from patients self-medicating with cannabis, suggest that cannabinoid receptor agonists may have a role in treating pain (Fox A, Bevan S., *Therapeutic potential of cannabinoid receptor agonists as analgesic agents*. Expert Opin Investig Drugs, 2005, 14, 695-703). G W Sativex, a 1:1 ratio of $\Delta^9$-THC and cannabidiol in an oromucosal spray formulation that allows individualised dosing for the treatment of neuropathic pain has been launched by GW Pharmaceuticals. Clinical studies with Sativex have demonstrated efficacy in patients with intractable pain (chronic neuropathic pain, pain due to brachial plexus nerve injury, allodynic peripheral neuropathic pain and advanced cancer pain), rheumatoid arthritis and symptoms associated with multiple sclerosis (pain, spasticity, poor bladder control and disrupted sleep; (Barnes M P. 2006. *Sativex: clinical efficacy and tolerability in the treatment of symptoms of multiple sclerosis and neuropathic pain*. Expert Opin. Pharmacother. 7(5): 607-615).

Two types of cannabinoid receptors have been identified. The cannabinoid CB1 receptor is located primarily in the central nervous system (CNS; brain and spinal cord), but is also expressed by peripheral neurones and to a lower extent in other peripheral tissues. The cannabinoid CB2 receptor is mainly confined to the periphery, mostly in immune cells (Howlett, A. C. et al, International Union of Pharmacology. XXVII. *Classification of Cannabinoid Receptors*. Pharmacol. Rev. 54, 161-202, 2002). While the conventional CB1 receptor agonists and CB1/CB2 receptor agonists, such as tetrahydrocannabinol (THC) are highly effective in models of pain in animals, their therapeutic utility in man is limited by undesired CNS side-effects, such as psychoactive effects, and by abuse potential (Chapman, V. and Finn, D. P. "*Analgesic effects of cannabinoids: sites and mechanism of action*." Rev. Analg. 7, 25-39, 2003).

Recent literature evidence suggests that selective activation of the CB2 receptor may constitute a novel strategy for treating pain and inflammation without undesirable CNS side effects. (Guindon, J. and Hohmann, A., "*Cannabinoid CB2 receptors: a therapeutic target for the treatment of inflammatory and neuropathic pain*", Br. J. Pharmacol., 2008, 153, 319-334). Activation of the CB2 receptor was found to inhibit acute, inflammatory and neuropathic pain responses in animal models (Whiteside G. T., Lee G. P., Valenzano K. J. "*The role of the cannabinoid CB2 receptor in pain transmission and therapeutic potential of small molecule CB2 receptor agonists*, Current Med. Chem., 2007, 14, 917-936). CB2 knock-out mice studies also support a role for CB2 receptors in pain (Malan T P, Jr, Ibrahim M M, Lai J, Vanderah T W, Makriyannis A and Porreca F. *CB2 cannabinoid receptor agonists: pain relief without psychoactive effects*? Curr. Opin. Pharmacol. 2003; 3: 62-67).

The cellular mechanisms contributing to CB2-mediated antinociception are not yet clear, but it has been proposed that activation of CB2 receptors affects inflammatory pain indirectly via modulation of immune cell activity, resulting in decreased release of mediators at the local site of inflammation. In addition to a peripheral effect, recent publications suggest that CB2 receptor agonists can also interact with CB2 receptors expressed on peripheral neurons and activated microglia to modulate pain transmission (Beltramo et al., 2006. *CB2 receptor-mediated antihyperalgesia: possible direct involvement of neural mechanisms*. Eur J Neurosci.

23(6):1530-80; Romero-Sandoval & Eisenach, 2007. *Spinal cannabinoid receptor type 2 activation reduces hypersensitivity and spinal cord glial activation after paw incision.* Anesthesiology 106(4):787-94).

In summary, CB2 receptor agonists may be suitable for the treatment of acute and chronic pain conditions, such as osteoarthritis, rheumatoid arthritis and acute post-operative pain and neuropathic pain. The absence of catalepsy with CB2 agonists in preclinical models shows promise for the treatment of acute and chronic pain without undesired CNS side effects.

N-(Biphenyl-4-ylmethyl)piperidine, -morpholine and -piperazine derivatives have recently been disclosed in the International Patent Application WO 2007/070760 (Boehringer Ingelheim International) as CB2 modulators useful in the treatment of inflammatory diseases, autoimmune diseases and pain.

There remains a need for further selective CB2 cannabinoid receptor agonists as therapeutic agents in the treatment of pain.

SUMMARY OF THE INVENTION

To this end the present invention provides a novel structural class of 1-(biphenyl-4-ylmethyl)imidazolidine-2,4-dione derivatives having the general Formula I

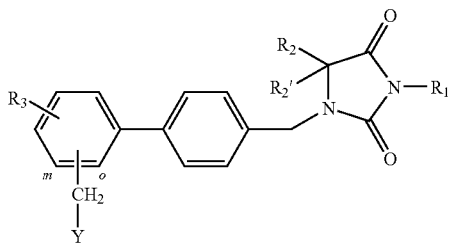

Formula I wherein
$R_1$ is H, $(C_{1-6})$alkyl (optionally substituted with oxo, $OR_4$, $COOR_5$, halogen or CN), $(C_{2-6})$alkenyl, $(C_{2-6})$alkynyl, $(C_{3-6})$cycloalkyl or $(C_{3-6})$cycloalkyl$(C_{1-3})$alkyl;
$R_2$ and $R_2'$ are independently H or $(C_{1-3})$alkyl; or
$R_2$ and $R_2'$ form together with the carbon atom to which they are bound a $(C_{3-5})$-cycloalkyl group;
$R_3$ represents H or 1 to 4 F substituents;
Y represents

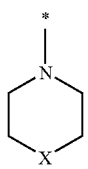

or $NR_8R_9$;
X represents $CHR_6$, $CF_2$, O, S, SO or $SO_2$;
$R_4$ and $R_5$ are $(C_{1-6})$alkyl;
$R_6$ is H, $OR_7$ or CN;
$R_7$ is $(C_{1-3})$alkyl;
$R_8$ is $(C_{5-7})$cycloalkyl comprising a heteroatom selected from O, S, SO and $SO_2$;
$R_9$ is H or $(C_{1-4})$alkyl;
o and m represent the ortho or meta position of the substituent Y—$CH_2$;

or a pharmaceutically acceptable salt thereof, as agonists of the cannabinoid CB2 receptor, which can be used in the treatment of pain such as for example peri-operative pain, chronic pain, neuropathic pain, cancer pain and pain and spasticity associated with multiple sclerosis.

Figure 1:
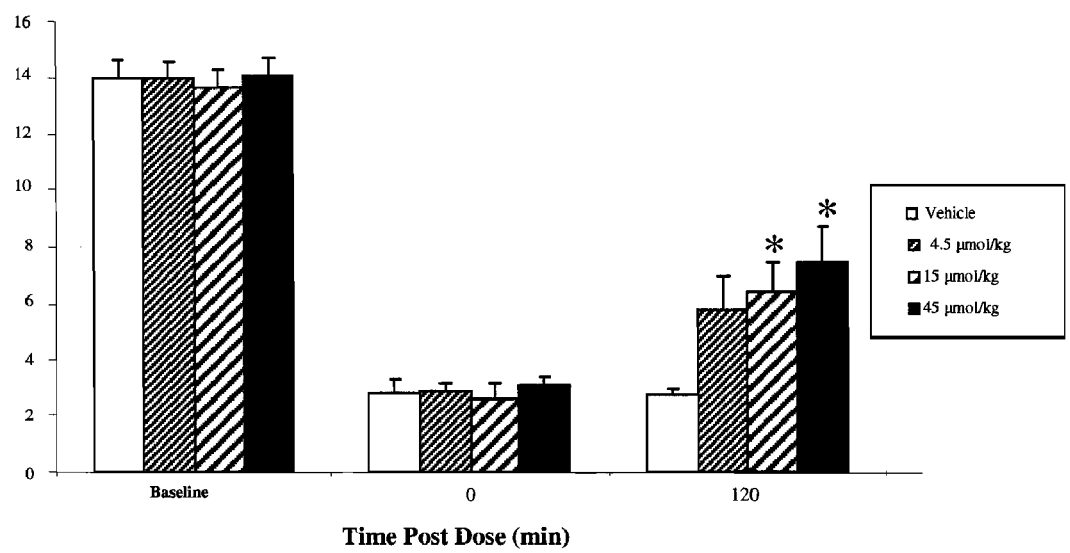
FIG. 1: The effect of acute oral administration of compound 3K on neuropathy-induced mechanical allodynia in rats.

The reading at 0 min denotes the post-surgery withdrawal threshold (the difference between the pre-surgery and 0 min reading denotes the development of mechanical allodynia), this reading was followed by administration of test compound. Data are expressed as mean±s.e.m.

DESCRIPTION OF THE INVENTION

The term $(C_{1-6})$alkyl as used in the definition of Formula I means a branched or unbranched alkyl group having 1-6 carbon atoms, like hexyl, pentyl, butyl, isobutyl, tertiary butyl, propyl, isopropyl, ethyl and methyl.

The term $(C_{1-3})$alkyl likewise means a branched or unbranched alkyl group having 1-3 carbon atoms, like propyl, isopropyl, ethyl and methyl.

The term $(C_{2-6})$alkenyl means a branched or unbranched alkenyl group having 2-6 carbon atoms, such as for example 4-hexenyl, but-2-enyl, 1-methylenepropyl, 2-propenyl(allyl) and ethenyl(vinyl).

The term $(C_{2-6})$alkynyl means a branched or unbranched alkynyl group, like 4-hexynyl, 2-butynyl and ethynyl.

The term $(C_{3-6})$cycloalkyl means a cycloalkyl group having 3-6 carbon atoms, like cyclohexyl, cyclopentyl, cyclobutyl and cyclopropyl.

The term $(C_{3-5})$cycloalkyl means a cycloalkyl group having 3-5 carbon atoms, like cyclopentyl, cyclobutyl and cyclopropyl.

The term $(C_{5-7})$cycloalkyl means a cycloalkyl group having 5-7 carbon atoms, like cyclopentyl, cyclohexyl and cycloheptyl.

The term halogen means F, Cl, Br or I. Preferred is F.

There is a preference for 1-(biphenyl-4-ylmethyl)imidazolidine-2,4-dione derivatives according to Formula I, wherein Y represents $NR_8R_9$ and $R_8$ is tetrahydropyran-4-yl or tetrahydrofuran-3-yl. More preferred are derivatives of Formula I wherein $R_3$ represents a para-fluoro substituent.

In one embodiment the present invention relates to the 1-(biphenyl-4-ylmethyl)-imidazolidine-2,4-dione derivative of claim 1 wherein Y represents

and wherein
$R_1$ is H, $(C_{1-6})$alkyl (optionally substituted with oxo, $OR_4$, $COOR_5$, halogen or CN), $(C_{2-6})$alkenyl, $(C_{2-6})$alkynyl, $(C_{3-6})$cycloalkyl or $(C_{3-6})$cycloalkyl$(C_{1-3})$alkyl;
$R_2$ and $R_2'$ are independently H or $(C_{1-3})$alkyl; or R$_2$ and R$_2$' form together with the carbon atom to which they are bound a (C$_{3-5}$)-cycloalkyl group;
R$_3$ represents H or 1 to 4 F substituents;
X represents CHR$_6$, CF$_2$, O, S, SO or SO$_2$;
R$_4$ and R$_5$ are (C$_{1-6}$)alkyl;
R$_6$ is H, OR$_7$ or CN;
R$_7$ is (C$_{1-3}$)alkyl;
o and m represent the ortho or meta position of the aminomethylene substituent;
or a pharmaceutically acceptable salt thereof.

In further preferred compounds of the invention according to this embodiment R$_1$ is (C$_{1-6}$)alkyl (optionally substituted with F), (C$_{3-6}$)cycloalkyl or (C$_{3-6}$)cycloalkyl(C$_{1-3}$)alkyl and R$_2$ and R$_2$' are H. More preferred are compounds, wherein X is CH$_2$, CF$_2$ or O.

Specifically preferred 1-(biphenyl-4-ylmethyl)imidazolidine-2,4-dione derivative of the invention are:
- 1-(2'-(morpholin-4-ylmethyl)biphenyl-4-ylmethyl)-3-propyl-imidazolidine-2,4-dione;
- 3-isobutyl-1-(2'-(morpholin-4-ylmethyl)biphenyl-4-ylmethyl)imidazolidine-2,4-dione;
- 3-butyl-1-(2'-(morpholin-4-ylmethyl)biphenyl-4-ylmethyl)imidazolidine-2,4-dione;
- 3-cyclobutylmethyl-1-(2'-(morpholin-4-ylmethyl)biphenyl-4-ylmethyl)imidazolidine-2,4-dione;
- 3-allyl-1-(2'-(morpholin-4-ylmethyl)biphenyl-4-ylmethyl)imidazolidine-2,4-dione;
- 1-(2'-(morpholin-4-ylmethyl)biphenyl-4-ylmethyl)-3-prop-2-ynyl-imidazolidine-2,4-dione;
- 3-(2,2-difluoro-ethyl)-1-(2'-(morpholin-4-ylmethyl)biphenyl-4-ylmethyl)imidazolidine-2,4-dione,
- 3-(2-fluoro-ethyl)-1-(2'-(morpholin-4-ylmethyl)biphenyl-4-ylmethyl)imidazolidine-2,4-dione;
- 3-(2-methoxy-ethyl)-1-(2'-(morpholin-4-ylmethyl)biphenyl-4-ylmethyl)imidazolidine-2,4-dione;
- 3-((2'-(morpholin-4-ylmethyl)biphenyl-4-ylmethyl)-2,5-dioxo-imidazolidin-1-yl)-acetic acid methyl ester;
- 1-(2'-(morpholin-4-ylmethyl)biphenyl-4-ylmethyl)-3-(2-oxo-butyl)imidazolidine-2,4-dione;
- 3-cyclopropylmethyl-1-(2'-(morpholin-4-ylmethyl)biphenyl-4-ylmethyl)imidazolidine-2,4-dione;
- 1-(3'-(4,4-difluoro-piperidin-1-ylmethyl)biphenyl-4-ylmethyl)imidazolidine-2,4-dione;
- 3-allyl-1-(3'-(4,4-difluoro-piperidin-1-ylmethyl)biphenyl-4-ylmethyl)imidazolidine-2,4-dione;
- 3-cyclobutylmethyl-1-(3'-(4,4-difluoro-piperidin-1-ylmethyl)biphenyl-4-ylmethyl)imidazolidine-2,4-dione;
- 3-cyclopropyl-1-(4'-fluoro-3'-(morpholin-4-ylmethyl)biphenyl-4-ylmethyl)imidazolidine-2,4-dione;
- 1-(4'-(3-cyclopropylmethyl-2,4-dioxo-imidazolidin-1-ylmethyl)biphenyl-2-ylmethyl)-piperidine-4-carbonitrile;
- 3-cyclopropylmethyl-1-(2'-(piperidin-1-ylmethyl)biphenyl-4-ylmethyl)imidazolidine-2,4-dione;
- 3-cyclopropyl-1-(3'-(thiomorpholin-4-ylmethyl)biphenyl-4-ylmethyl)imidazolidine-2,4-dione;
- 3-cyclopropyl-1-(3'-(1,1-dioxo-1λ$^6$-thiomorpholin-4-ylmethyl)biphenyl-4-ylmethyl)-imidazolidine-2,4-dione;
- 3-isobutyl-1-(3'-(piperidin-1-ylmethyl)biphenyl-4-ylmethyl)imidazolidine-2,4-dione;
- 1-(4'-fluoro-3'-(morpholin-4-ylmethyl)biphenyl-4-ylmethyl)-3-isobutyl-imidazolidine-2,4-dione;
- 1-(3'-fluoro-5'-(morpholin-4-ylmethyl)biphenyl-4-ylmethyl)-3-isobutyl-imidazolidine-2,4-dione;
- 1-(2'-fluoro-3'-(morpholin-4-ylmethyl)biphenyl-4-ylmethyl)-3-isobutyl-imidazolidine-2,4-dione;
- 3-cyclobutylmethyl-1-(3'-(piperidin-1-ylmethyl)biphenyl-4-ylmethyl)imidazolidine-2,4-dione;
- 3-(2,2-difluoro-ethyl)-1-(3'-(piperidin-1-ylmethyl)biphenyl-4-ylmethyl)-imidazolidine-2,4-dione;
- 1-(4'-fluoro-3'-(piperidin-1-ylmethyl)biphenyl-4-ylmethyl)-3-isobutyl-imidazolidine-2,4-dione;
- 3-(2,2-difluoro-ethyl)-1-(2'-fluoro-3'-(piperidin-1-ylmethyl)biphenyl-4-ylmethyl)-imidazolidine-2,4-dione;
- 1-(2'-fluoro-3'-(piperidin-1-ylmethyl)biphenyl-4-ylmethyl)-3-isobutyl-imidazolidine-2,4-dione;
- 1-(3'-fluoro-5'-(piperidin-1-ylmethyl)biphenyl-4-ylmethyl)-3-isobutyl-imidazolidine-2,4-dione;
- 1-(3'-(1,1-dioxo-1λ$^6$-thiomorpholin-4-ylmethyl)-4'-fluoro-biphenyl-4-ylmethyl)-3-isobutyl-imidazolidine-2,4-dione;
- 3-cyclopropylmethyl-1-(3'-(1,1-dioxo-1λ$^6$-thiomorpholin-4-ylmethyl)biphenyl-4-ylmethyl)imidazolidine-2,4-dione;
- 3-cyclopropylmethyl-1-(3'-(1,1-dioxo-1λ$^6$-thiomorpholin-4-ylmethyl)-4'-fluoro-biphenyl-4-ylmethyl)imidazolidine-2,4-dione;
- 1-(3'-(1,1-dioxo-1λ$^6$-thiomorpholin-4-ylmethyl)biphenyl-4-ylmethyl)-3-isobutyl-imidazolidine-2,4-dione;
- 3-cyclobutyl-1-((4'-fluoro-3'-(thiomorpholinomethyl)biphenyl-4-yl)methyl)imidazolidine-2,4-dione;
- 3-cyclobutyl-1-(3'-(1,1-dioxo-1λ$^6$-thiomorpholin-4-ylmethyl)biphenyl-4-ylmethyl)imidazolidine-2,4-dione;
- 3-cyclobutyl-1-(3'-(1,1-dioxo-1λ$^6$-thiomorpholin-4-ylmethyl)-4'-fluoro-biphenyl-4-ylmethyl)imidazolidine-2,4-dione;
- 3-cyclopropyl-1-(3'-(1,1-dioxo-1λ$^6$-thiomorpholin-4-yl-methyl)biphenyl-4-ylmethyl)imidazolidine-2,4-dione;
- (S)-3-(cyclopropylmethyl)-1-((4'-fluoro-3'-((tetrahydrofuran-3-ylamino)methyl)biphenyl-4-yl)methyl)imidazolidine-2,4-dione;
- (R)-3-(cyclopropylmethyl)-1-((4'-fluoro-3'-((tetrahydrofuran-3-ylamino)methyl)biphenyl-4-yl)methyl)imidazolidine-2,4-dione;
- 3-(cyclopropylmethyl)-1-((4'-fluoro-3'-((tetrahydro-2H-pyran-4-ylamino)methyl)biphenyl-4-yl)methyl)imidazolidine-2,4-dione;
- 1-((3'-((tetrahydro-2H-pyran-4-ylamino)methyl)biphenyl-4-yl)methyl)-3-(2,2,2-trifluoroethyl)imidazolidine-2,4-dione;
- (R)-1-((4'-fluoro-3'-((tetrahydrofuran-3-ylamino)methyl)biphenyl-4-yl)methyl)-3-(2,2,2-trifluoroethyl)imidazolidine-2,4-dione;
- (S)-1-((4'-fluoro-3'-((tetrahydrofuran-3-ylamino)methyl)biphenyl-4-yl)methyl)-3-(2,2,2-trifluoroethyl)imidazolidine-2,4-dione;
- (R)-1-((4'-fluoro-3'-((tetrahydrofuran-3-ylamino)methyl)biphenyl-4-yl)methyl)-3-isopropylimidazolidine-2,4-dione;
- 1-((4'-fluoro-3'-((tetrahydro-2H-pyran-4-ylamino)methyl)biphenyl-4-yl)methyl)-3-isopropylimidazolidine-2,4-dione;
- (S)-1-((4'-fluoro-3'-((tetrahydrofuran-3-ylamino)methyl)biphenyl-4-yl)methyl)-3-isopropylimidazolidine-2,4-dione; and
- 1-((4'-fluoro-3'-((tetrahydro-2H-pyran-4-ylamino)methyl)biphenyl-4-yl)methyl)-3-(2,2,2-trifluoroethyl)imidazolidine-2,4-dione or a pharmaceutically acceptable salt thereof.

The 1-(biphenyl-4-ylmethyl)imidazolidine-2,4-dione derivatives (1) of the invention may be prepared by methods known in the art of organic chemistry in general.

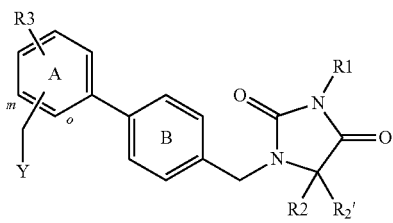

The imidazolidine-2,4-dione ring in the compounds of Formula I (1) can for instance be derived from the appropriate amino acid H$_2$N—C(R$_2$,R$_2$')—COOH, wherein R$_2$ and R$_2$' have the meaning as previously defined, or from an amide derivative 4 thereof (Scheme 1).

Scheme 1. Preparation of amino acid derivatives.

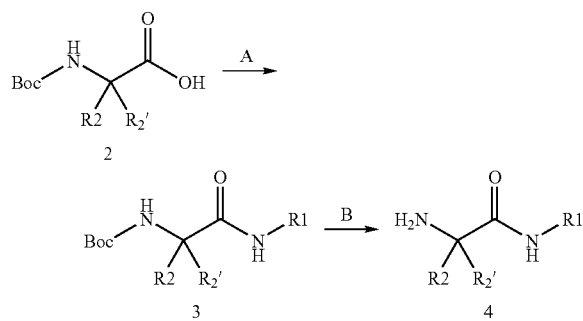

Conditions:

A: R$_1$NH$_2$/TBTU/DIPEA B: TFA or HCl

Compounds of formula 4 can be obtained from the condensation of a N-tert-butyloxy carbonyl-(Boc)-protected amino acid derivative of formula 2 with an appropriate amine of formula R$_1$—NH$_2$ using an amide bond forming reagent, such as dicyclohexylcarbodiimide (DCCI), TBTU or PyBOP or the like, to the Boc-protected amino acid amide derivative of formula 3, from which the Boc group is removed by a treatment with trifluoroacetic acid or with hydrochloric acid in an organic solvent.

Compounds of the invention can for instance be prepared, as depicted in Scheme 2, by coupling of the amino acid H$_2$N—C(R$_2$,R$_2$')—COOH with 4-bromobenzaldehyde (5) under reductive amination conditions to obtain the N-benzyl derivative of the amino acid of formula 6, which is subsequently coupled with the amine H$_2$N—R$_1$, wherein R$_1$ has the previously defined meaning, with the aid of an amide bond forming reagent (supra) to the amide derivative 7, from which the imidazolidine-2,4-dione derivative 8 can be prepared by a ring closure reaction using carbonyldiimidazole. A subsequent Suzuki coupling of a compound of formula 8 with an appropriate formylphenylboronic acid derivative provides an ortho- or meta-formyl-1-(biphenyl-4-ylmethyl)imidazolidine-2,4-dione derivative of formula 9, which can be converted to a compound of the invention by coupling to an amine Y—H, wherein Y has the meaning as previously defined, under reductive amination conditions.

Scheme 2.

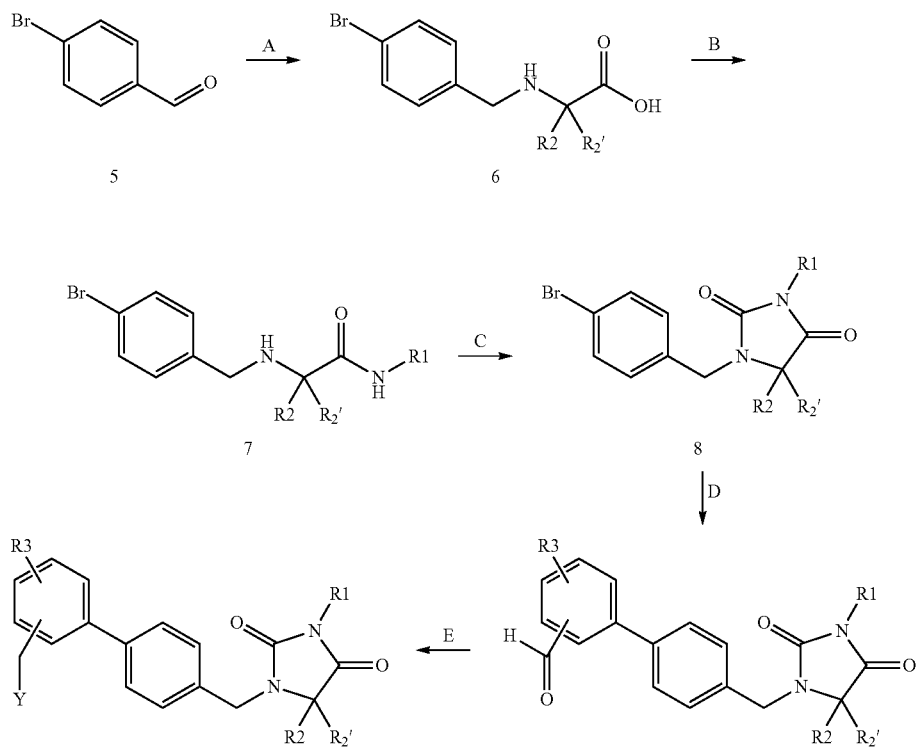

Conditions:

A: compound 4/sodium hydroxide/sodium borohydride or triacetoxyborohydride. B: R₁NH₂/triethylamine/PyBOP. C: CDI/DMAP. D: formylphenylboronic acid/sodium hydrogen carbonate/(Ph₃P)₄Pd. E: Y—H/triethylamine/sodium borohydride or sodium triacetoxyborohydride.

An alternative synthetic route for the preparation of compounds of formula 1 of the invention is depicted in Scheme 3. In this route the final step is the ringclosure reaction of the amino acid derivative 17 with the aid of carbonyldiimidazole. Amino acid derivatives 17 can be prepared from the reductive amination of amino acid derivatives of formula 4 (Scheme 1) by a 4-phenylbenzaldehyde derivative of formula 13.

formula 13 can be prepared starting from the reaction of an amine of formula Y—H with a bromobenzylbromide of formula 14, to yield a bromophenylderivative of formula 16, which is subsequently reacted in a Suzuki coupling reaction with 4-formylphenyl-boronic acid. Compound 16 can also be obtained from reacting the corresponding bromobenzaldehyde 15 with an amine of formula Y—H under reductive amination conditions.

Compounds of the invention wherein R₁ is hydrogen (23), can be prepared as depicted in Scheme 4, starting with the reductive amination of an amino acid ester derivative of formula H₂N—C(R₂,R₂')—COOMe by a 4-phenylbenzaldehyde derivative of formula 13, to the methyl-2-(biphenyl-4-

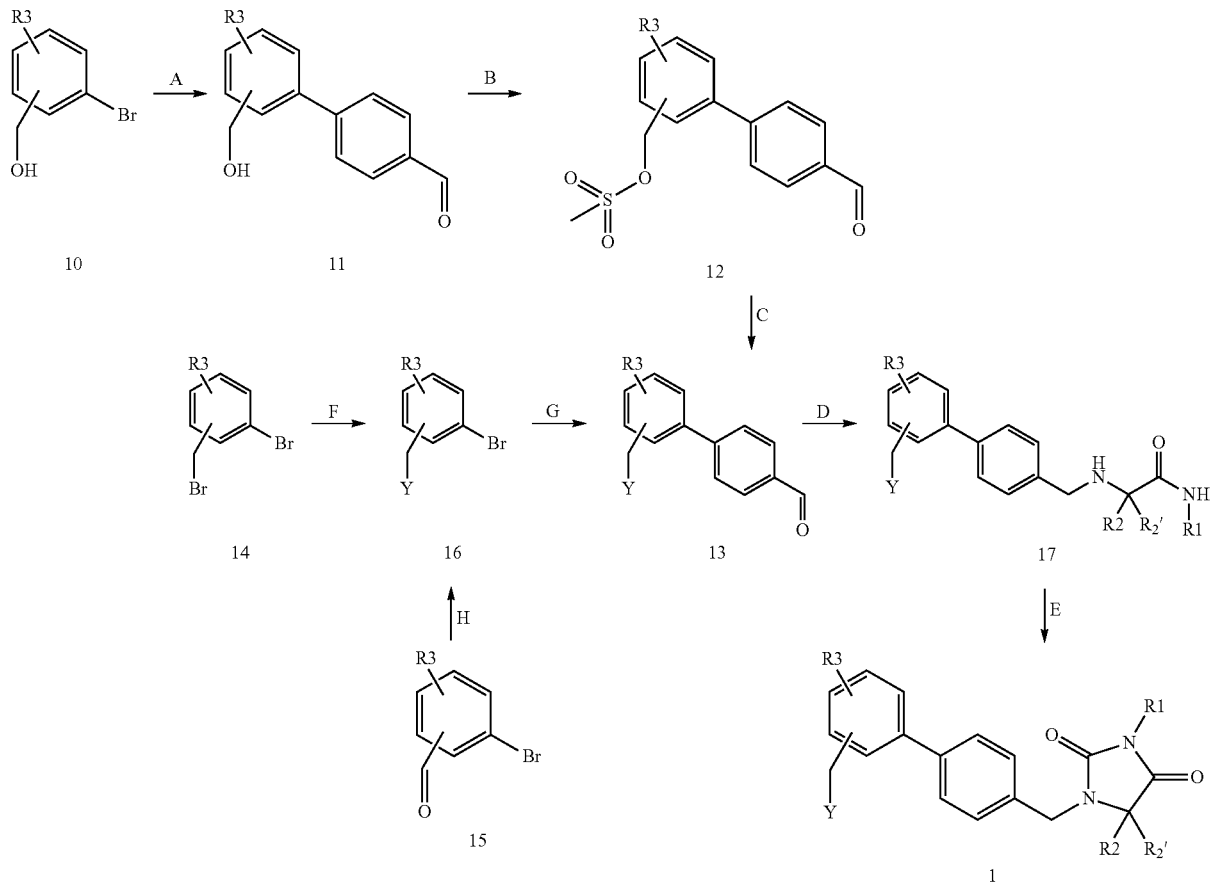

Scheme 3.

ylmethylamino)acetate derivate of formula 24, after which the unsubstituted imidazolidine-2,4-dione ring can be obtained following reaction with potassium isocyanate to the intermediate carbamoyl-derivative 25 and subsequent ring closure using sodium methoxide. In an alternative route, the unsubstituted imidazolidine-2,4-dione ring can be introduced early on at the stage of the 4-bromobenzylated amino acid ester derivative of formula 19 by carbamoylation with isocyanate to the intermediate 20 and the ring closure reaction to give the 1-(4-bromobenzyl)imidazolidine-2,4-dione derivative 21, after which the substituted biphenyl moiety can be built up using the above described Suzuki coupling reaction to intermediate 22 and the introduction of the amine moiety Y by reductive amination. The resulting compounds of the invention according to formula 23 can be used to prepare further compounds of Formula I by alkylation with the appropriate R₁-halogenides.

Conditions:

A: 4-formylphenylboronic acid/sodium hydrogen carbonate/(Ph₃P)₄Pd. B: methanesulfonyl chloride/DIPEA. C: HN(CH₂—CH₂)₂X. D: compound 4/acetic acid/sodium borohydride or sodium triacetoxyborohydride. E: CDI/DMAP. F: potassium carbonate/Y—H. G: 4-formylphenylboronic acid/sodium hydrogen carbonate/(Ph₃P)₄Pd. H: Y—H/Et₃N/sodium triacetoxyborohydride.

Compounds of formula 13 can be prepared from the substitution reaction of a mesylate of formula 12 with an amine of formula Y—H. The mesylate of structure 12 can be obtained from reacting the corresponding benzylalcohol derivative of formula 11 with methanesulfonylchloride. Compounds 11 may be obtained from a Suzuki coupling reaction of the bromobenzylalcohol derivatives of structure 10 with 4-formylboronic acid. In an alternative manner compounds of

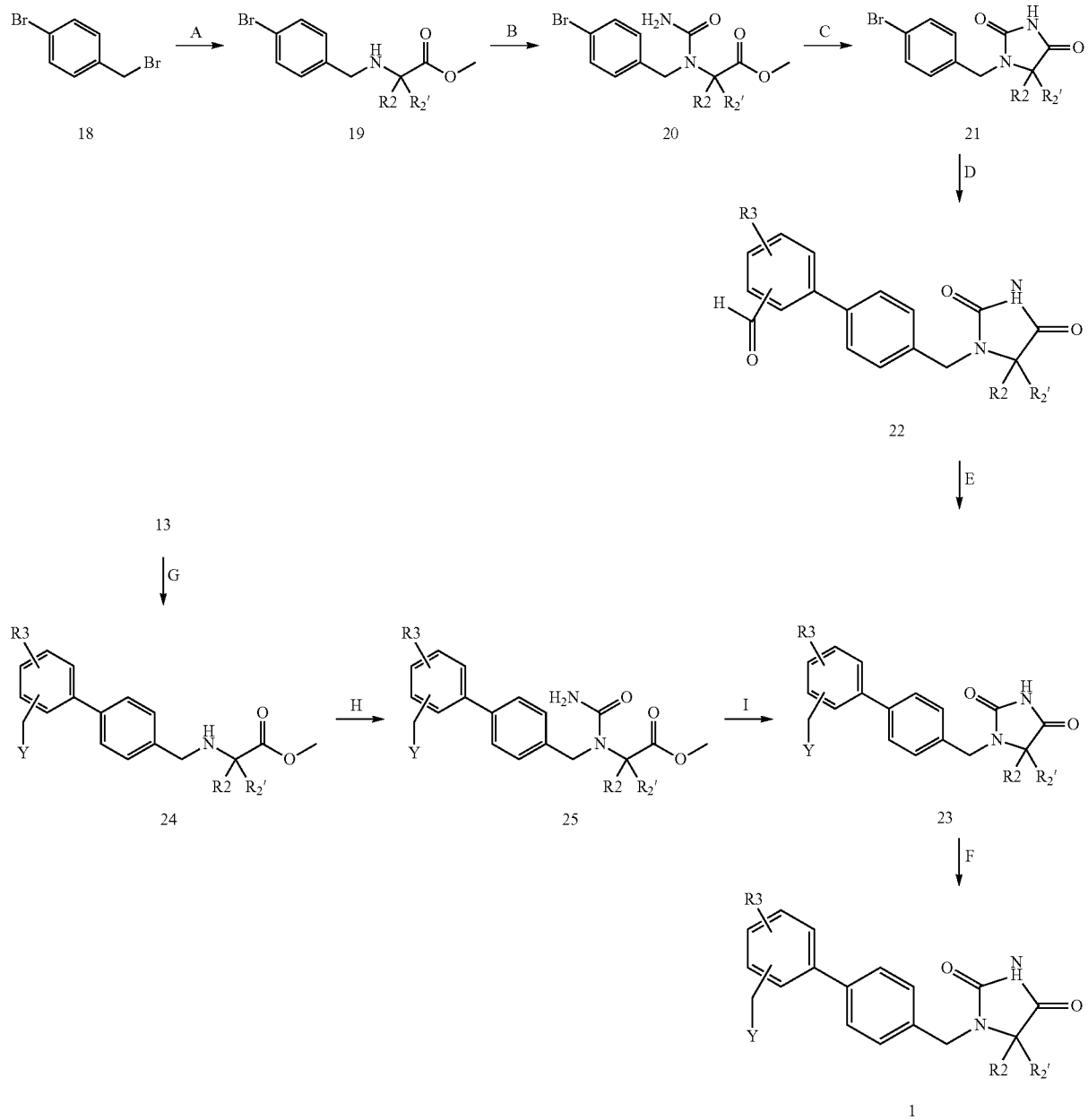

Scheme 4.

Conditions:

A: H$_2$N—C(R$_2$,R$_2$')—COOMe hydrochloride/potassium carbonate/tetrabutylammonium sulfate. B: potassium isocyanate/acetic acid. C: sodium methoxide. D: formylphenylboronic acid/sodium hydrogen carbonate/(Ph$_3$P)$_4$Pd. E: Y—H/acetic acid/sodium triacetoxyborohydride. F: R$_1$-halide/potassium carbonate. G: H$_2$N—C(R$_2$,R$_2$')—COOMe hydrochloride/sodium triacetoxyborohydride or sodium borohydride. H: potassium isocyanate/acetic acid I: sodium methoxide.

In an alternative synthesis route (Scheme 5), the introduction of substituent R$_1$ in the compounds 1 of the invention can be carried out by alkylation of the intermediate 21 to the alkylated imidazolidine of formula 8, followed by a Suzuki coupling reaction to intermediate 9 and the introduction of the amine moiety Y by reductive amination.

Scheme 5 also shows a synthesis route wherein the amine moiety Y is introduced in an early stage of the synthesis by a reductive amination reaction using amine Y—H and the formylphenylboronic acid derivative 26 to provide the intermediate 27, from which a compound 1 of the invention is obtained following a subsequent Suzuki coupling reaction with an imidazolidine of formula 8.

Scheme 5.

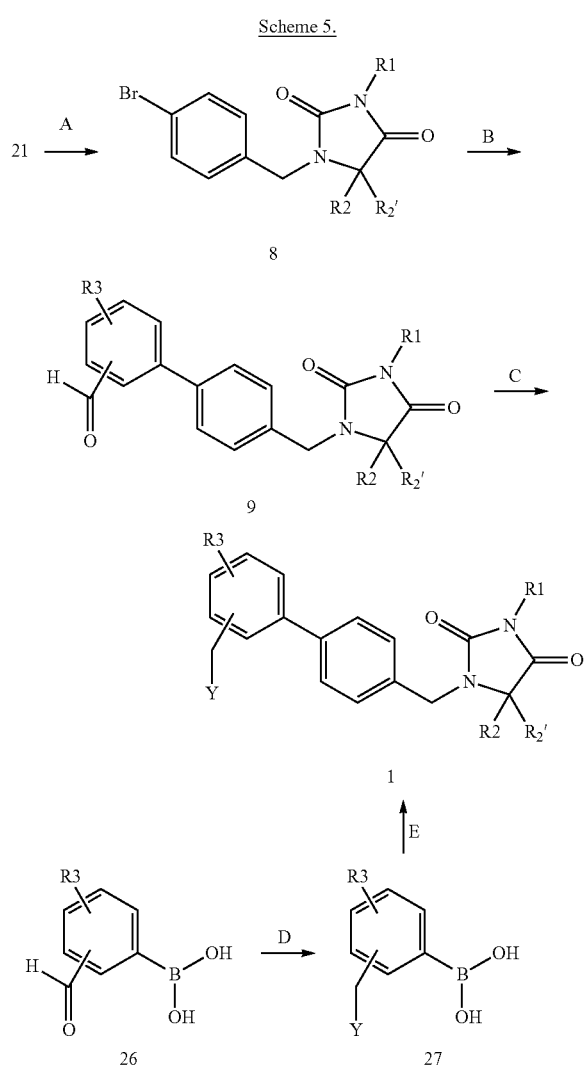

Conditions:

A: R₁-halide/potassium carbonate. B: formylphenylboronic acid/sodium hydrogen carbonate/(Ph₃P)₄Pd. C: Y—H/acetic acid/sodium triacetoxyborohydride. D: Y—H/acetic acid/sodium triacetoxyborohydride. E: Compound 8/potassium carbonate/(Ph₃P)₄Pd.

Scheme 6.

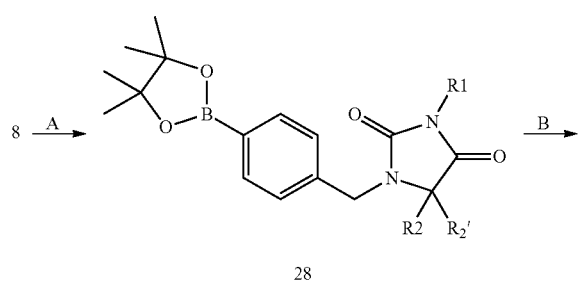

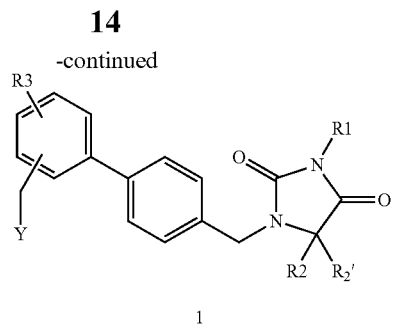

Conditions:

A: bis(pinacolato)diboron/potassium acetate/1,1'-bis(diphenylphosphino)ferrocene palladium (ii) chloride, complex with CH₂Cl₂. B: compound 16,/potassium carbonate/(Ph₃P)₄Pd.

Scheme 6 further depicts a route wherein a boronic ester functionality is introduced into the phenylmethylimidazolidine of formula 8 to yield the intermediate compound of formula 28, from which a compound 1 of the invention is obtained from a subsequent Suzuki coupling reaction with a bromophenyl derivative of formula 16 (Scheme 3).

The 1-(biphenyl-4-ylmethyl)imidazolidine-2,4-dione derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free base, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis or chiral separation whereby the pure stereo-isomers are obtained are well known in the art, e.g. synthesis with chiral induction or starting from commercially available chiral substrates, or separation of stereo-isomers, for example using chromatography on chiral media or by crystallisation with a chiral counter-ion.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a 1-(biphenyl-4-ylmethyl)imidazolidine-2,4-dione derivative according to general Formula I, or a pharmaceutically acceptable salt thereof, in admixture with one or more pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, ocular or rectal administration, and the like, all in unit dosage forms for administration. A preferred route of administration is the oral route.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al, Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting, agents, such as propylene glycol or butylene glycol. The invention further includes a pharmaceutical composition, as described before, in combination with packaging material suitable for said composition, said packaging material including instructions for the use of the composition for the use as described before.

The 1-(biphenyl-4-ylmethyl)imidazolidine-2,4-dione derivatives of the invention were found to be selective agonists of the CB2 receptor as compared to the CB1 receptor, as determined in a human CB2 and CB1 reporter assays using CHO cells. Methods to determine receptor binding as well as in vitro biological activity of cannabinoid receptor modulators are well known in the art. In general, expressed receptor is incubated with the compound to be tested and binding or stimulation or inhibition of a functional response is measured.

To measure a functional response isolated DNA encoding the CB2 or CB1 receptor gene, preferably the human receptor, is expressed in suitable host cells. Such a cell might be the Chinese Hamster Ovary cell, but other cells are also suitable. Preferably the cells are of mammalian origin.

Methods to construct recombinant CB2 or CB1 expressing cell lines are well known in the art (Sambrook et al, Molecular Cloning: a Laboratory Manual, Cold Spring Harbor Laboratory Press, Cold Spring Harbor, latest edition). Expression of the receptor is attained by expression of the DNA encoding the desired protein.

Techniques for ligation of additional sequences and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then incubated with the test compound to observe binding, or stimulation or inhibition of a functional response.

Alternatively isolated cell membranes containing the expressed CB2 or the CB1 receptor may be used to measure binding of compound.

For measurement of binding radioactively or fluorescently labelled compounds may be used. The most widely used radiolabelled cannabinoid probe is ($^3$H)CP55940, which has approximately equal affinity for CB1 and CB2 binding sites.

Functional CB2 or CB1 agonist activity may be measured by determining the second messenger response, such as for example measurement of receptor mediated changes in cAMP or MAP kinase pathways. Thus, such a method involves expression of the CB2 or CB1 receptor on the cell surface of a host cell and exposing the cell to the test compound. The second messenger response is then measured. The level of second messenger will be reduced or increased, depending on the effect of the test compound upon binding to the receptor.

In addition to direct measurement of e.g. cAMP levels in the exposed cell, cells can be used which in addition to transfection with receptor encoding DNA are also transfected with a second DNA encoding a reporter gene, the expression of which correlates with receptor activation. In general, reporter gene expression might be controlled by any response element reacting to changing levels of second messenger. Suitable reporter genes are e.g. LacZ, alkaline phosphatase, firefly luciferase and green fluorescence protein. The principles of such transactivation assays are well known in the art and are described e.g. in Stratowa, C., Himmler, A. and Czernilofsky, A. P., *Curr. Opin. Biotechnol.* 6, 574 (1995). For selecting selective, active agonist compounds on the CB2 receptor the $EC_{50}$ value for a compound is $<10^{-5}$ M, preferably $<10^{-7}$ M and the selectivity over CB1 receptor agonist as defined as EC50 (CB1)/EC50 (CB2) is >10, preferably >50.

The compounds may be used as analgesic agents in the treatment of pain such as for example acute pain such as peri-operative pain, chronic pain, neuropathic pain, cancer pain, visceral pain, headache and spasticity associated with multiple sclerosis.

Cannabinoid agonists of the invention would also potentially be useful in the treatment of other disorders including, (intestinal) inflammation, liver diseases, respiratory disorders, allergies, oncology, epilepsy, migraine, osteoporosis, cardiovascular disorders, acute neurodegenerative disorders, such as traumatic brain injury and stroke and slowly neurodegenerative disorders, such as Alzheimer's disease, multiple sclerosis and ALS (Parcher P, Batkai S, Kunos, G, The endocannabinoid system as an emerging target of pharmacotherapy, Pharmacol Rev. 2006, 58(3):389-462).

The compounds could also be used in conjunction with other drugs, for example analgesic drugs such as opioids and non-steroidal anti-inflammatory drugs (NSAIDs), including COX-2 selective inhibitors.

The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

The invention is illustrated by the following Examples.

Abbreviations: Boc: tert-butoxycarbonyl; $CDCl_3$: chloroform-d; DBU: 1,8-diazabicyclo(5.4.0)undec-7-ene; CDI: N,N'-carbonyldiimidazole; DCCI: 1,3-dicyclohexylcarbodiimide; DCM: dichloromethane; DIPEA: N,N-diisopropylethylamine; DMAP: 4-dimethylaminopyridine; DMF: N,N-dimethylformamide; $Et_3N$ or TEA: triethyl amine; Gly: glycinyl; HPLC: high performance liquid chromatography; HOAc: acetic acid; HOBt: 1-hydroxybenzo-triazole; MeOH:

methanol; Me₃SiCl or TMSCI: chlorotrimethylsilane; MS: mass spectrum; (PPh₃)₄Pd: tetrakis(triphenylphosphine)palladium(0); PyBOP: (benzotriazol-1-yloxy)tripyrrolidinophosphonium hexafluorophosphate; PyBrOP: bromo(tris pyrrolidino)phosphonium tetrafluorohosphate; TBTU: ((benzotriazol-1-yloxy)-dimethylamino-methylene)-dimethyl-ammonium tetrafluoro borate; TFA: trifluoroacetic acid; THF: tetrahydrofuran; TLC: thin layer chromatography.

EXAMPLE 1A

2-Amino-N-cyclopropyl-acetamide hydrochloride i)—TBTU (5.1 g, 16.5 mmol), DIPEA (2.9 ml, 16.5 mmol) and cyclopropylamine (2.2 ml, 33 mmol) were added to a solution of BOC-Gly-OH (2.63 g, 15 mmol) in dry dichloromethane (10 ml). After 17 h stirring, the reaction mixture was concentrated under reduced pressure and water was added to the residue. The product was extracted into ethyl acetate. The combined organic phases were washed with an aqueous solution of 2M hydrochloric acid, a saturated aqueous solution of sodium hydrogen carbonate, brine, dried over sodium sulfate and concentrated under reduced pressure to give 2-cyclopropylcarbamoylmethyl-carbamic acid tert-butyl ester (847 mg). The product was used in the following step without further purification.

ii)—An aqueous solution of 2M hydrochloric acid (10 ml) was added to a solution of the product obtained in the previous step (2.2 g, 10.3 mmol) in dioxane (25 ml). After 2 h stirring the reaction mixture was concentrated under reduced pressure. Crystallization from methanol/diethyl ether afforded 2-amino-N-cyclopropyl-acetamide hydrochloride (1.3 g). ¹H NMR (400 MHz, MeOD): δ 3.62 (s, 2H), 2.76-2.74 (m, 1H), 0.75 (m, 2H), 0.52 (m, 2H).

EXAMPLE 1B

2-Amino-N-cyclopropylmethyl-acetamide trifluoroacetate

The title was compound prepared from tert-Butoxycarbonylamino-acetic acid, using aminomethylcyclopropane and TFA, following procedures analogous to that described in Example 1A.
¹H-NMR (400 MHz, CDCl₃): δ 8.27 (s, 1H), 8.17 (s, 2H), 3.88 (s, 2H), 3.12 (d, J=6.8 Hz, 2H), 0.99 (m, 1H), 0.53 (m, 2H), 0.23 (m, 2H).

EXAMPLE 2

1-(2'-(Morpholin-4-ylmethyl)biphenyl-4-ylmethyl)-3-propyl-imidazolidine-2,4-dione

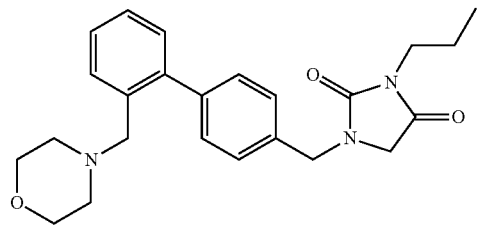

i)—To a solution of 2-bromo-benzylalcohol (5 g, 26.7 mmol) in 2-methoxyethanol/water (30 ml, 1/1) were added 4-formylphenylboronic acid (6 g, 40.0 mmol) and sodium bicarbonate (4.4 g, 52.4 mmol) under a nitrogen atmosphere. After (Ph₃P)₄Pd (1.54 g, 1.34 mmol) was added, the reaction mixture was heated under reflux for 17 h. After cooling, the mixture was filtered over dicalite and the residue was washed with water and ethyl acetate. The product was extracted into ethyl acetate. The combined organic phases were washed with brine, dried over magnesium sulfate concentrated under reduced pressure. Column chromatography afforded 2'-hydroxymethyl-biphenyl-4-carbaldehyde (3.95 g).

ii)—A solution of the product obtained in the previous step (2 g, 9.4 mmol) in dry dichloromethane (100 ml) evacuated and flushed with nitrogen 2 times. The solution was cooled to −15° C. under nitrogen. Methanesulfonylchloride (0.73 ml, 9.4 mmol) and N,N-diisopropylethylamine (1.65 ml, 9.4 mmol) were added and the reaction mixture was stirred for 10 minutes at −15° C., followed by 2 h at 0° C. Water was added and the product was extracted into dichloromethane. The combined organic phases were dried over magnesium sulfate and concentrated under reduced pressure to afford methanesulfonic acid 4'-formyl-biphenyl-2-yl methyl ester (2.85 g). The product was used in the following step without further purification.

iii)—A solution of the product obtained in the previous step (2.85 g, 9.8 mmol) and morpholine (3.46 ml, 39.3 mmol) in dry dioxane (180 ml) was stirred at 50° C. for 6 h. After cooling to room temperature, the reaction mixture was concentrated under reduced pressure. Column chromatography afforded 2'-morpholin-4-ylmethyl-biphenyl-4-carbaldehyde (2.32 g).

iv)—A solution of glycine methyl ester hydrochloride (0.29 g, 2.31 mmol) in dry methanol (7.5 ml) was added dropwise to a solution of the product obtained in the previous step (0.5 g, 1.78 mmol) in THF (7.5 ml). After 10 minutes stirring at room temperature, sodium triacetoxy borohydride was added. After 17 h stirring at room temperature the reaction mixture was quenched by addition of a saturated aqueous solution of sodium hydrogen carbonate and the product was extracted into ethyl acetate. The combined organic phases were washed with water, brine, dried over sodium sulfate and concentrated under reduced pressure. Column chromatography afforded (2'-((morpholin-4-ylmethyl)biphenyl-4-ylmethyl)amino)acetic acid methyl ester (338 mg).

v)—To a suspension of the product obtained in the previous step (715 mg, 2.02 mmol) in dioxane/water (11 ml, 1:1) were added potassium isocyanate (245 mg, 3.03 mmol) and acetic acid (0.37 ml, 6.46 mmol). After 2.5 h stirring at room temperature the reaction mixture was quenched by addition of water. The aqueous phase was neutralized with a saturated aqueous solution of sodium hydrogen carbonate and the product was extracted into ethyl acetate. The combined organic phases were washed with brine, dried over sodium sulfate and concentrated under reduced pressure to afford (1-(2'-(morpholin-4-ylmethyl)biphenyl-4-ylmethyl)ureido)acetic acid methyl ester (714 mg). The product was used in the following step without further purification.

vi)—Sodium methoxide (108 mg, 1.99 mmol) was added to a solution of the product obtained in the previous step (396 mg, 1.0 mmol) in dry methanol (7 ml). After 5 h stirring at room temperature the reaction mixture was quenched by addition of water and neutralized with a saturated aqueous solution of ammonium chloride. The product was extracted into ethyl acetate. The combined organic phases were washed with brine, dried over sodium sulfate and concentrated under reduced pressure. Column chromatography afforded 1-(2'-(morpholin-4-ylmethyl)biphenyl-4-ylmethyl)imidazolidine-2,4-dione (304 mg).

vii)—Potassium carbonate (85 mg, 0.62 mmol) and 1-bromopropane (50.5 mg, 0.41 mmol) were added to a solution of the product obtained in the previous step (75 mg, 0.20 mmol) in DMF (2 ml). After 20 h stirring at room temperature the reaction mixture was quenched by addition of water and the product was extracted into ethyl acetate. The combined organic phases were washed with water, brine, dried over sodium sulfate and concentrated under reduced pressure. Preparative HPLC afforded 1-(2'-(morpholin-4-ylmethyl)biphenyl-4-ylmethyl)-3-propyl-imidazolidine-2,4-dione (30.1 mg), $^1$H-NMR (400 MHz, CDCl$_3$): δ 7.52 (m, 1H), 7.42 (m, 2H), 7.22-7.38 (m, 5H), 4.62 (s, 2H), 3.80 (s, 2H), 3.64 (t, J=4.7 Hz, 4H), 3.52 (m, 2H), 3.38 (s, 2H), 2.38 (t, J=4.8 Hz, 4H), 1.65-1.73 (m, 2H), 0.98 (t, J=7.1 Hz, 3H).

EXAMPLE 3

Following a procedure analogous to that described in Example 2, step vii, using 1-(2'-morpholin-4-ylmethyl-biphenyl-4-ylmethyl)imidazolidine-2,4-dione (Example 2, step vi) as starting material, the following compounds were prepared.

3A

3-Isobutyl-1-(2'-(morpholin-4-ylmethyl)biphenyl-4-ylmethyl)imidazolidine-2,4-dione $^1$H-NMR (400 MHz, CDCl$_3$): δ 7.42 (m, 2H), 7.21-7.38 (m, 5H), 7.52 (m, 1H), 4.62 (s, 2H), 3.82 (s, 2H), 3.65 (t, J=4.6 Hz, 4H), 3.39 (d, 2H), 3.38 (s, 2H), 2.38 (t, J=4.3 Hz, 4H), 2.04-2.19 (m, 1H), 0.94 (d, J=6.6 Hz, 4H).

3B

3-Butyl-1-(2'-(morpholin-4-ylmethyl)biphenyl-4-ylmethyl)imidazolidine-2,4-dione $^1$H-NMR (400 MHz, CDCl$_3$): δ 7.52 (m, 1H), 7.42 (m, 2H), 7.22-7.36 (m, 5H), 4.62 (s, 2H), 3.80 (s, 2H), 3.66 (t, J=4.6 Hz, 4H), 3.57 (t, J=7.2 Hz, 2H), 3.38 (s, 2H), 2.38 (t, J=4.6 Hz, 4H), 1.55-1.69 (m, 2H), 1.31-1.42 (m, 2H), 0.96 (t, J=7.2 Hz, 3H).

3C

3-Cyclobutylmethyl-1-(2'-(morpholin-4-ylmethyl)biphenyl-4-ylmethyl)imidazolidine-2,4-dione $^1$H-NMR (400 MHz, CDCl$_3$): δ 7.52 (m, 1H), 7.41 (m, 2H), 7.21-7.38 (m, 5H), 4.62 (s, 2H), 3.79 (s, 2H), 3.65 (t, J=4.5 Hz, 4H), 3.59 (d, J=7.3 Hz, 2H), 3.38 (s, 2H), 2.67-2.79 (m, 1H), 2.38 (t, J=4.3 Hz, 4H), 2.01-2.19 (m, 2H), 1.76-1.92 (m, 4H).

3D

3-Allyl-1-(2'-(morpholin-4-ylmethyl)biphenyl-4-ylmethyl)imidazolidine-2,4-dione $^1$H-NMR (400 MHz, CDCl$_3$): δ 7.53 (m, 1H), 7.40 (m, 2H), 7.22-7.37 (m, 5H), 5.82-5.94 (m, 1H), 5.21-5.31 (m, 2H), 4.63 (s, 2H), 4.19 (t, J=1.1 Hz, 2H), 3.81 (s, 2H) 3.64 (t, J=4.7 Hz, 4H), 3.38 (s, 2H), 2.38 (t, J=4.6 Hz, 4H).

3E 1-(2'-Morpholin-4-ylmethyl-biphenyl-4-ylmethyl)-3-prop-2-ynyl-imidazolidine-2,4-dione $^1$H-NMR (400 MHz, CDCl$_3$): δ 7.51 (m, 1H), 7.42 (m, 2H), 7.22-7.36 (m, 5H), 4.63 (s, 2H), 4.34 (d, J=2.5 Hz, 2H), 3.83 (s, 2H), 3.63 (t, J=4.4 Hz, 4H), 3.38 (s, 2H), 2.38 (t, J=4.2 Hz, 4H), 2.27 (t, J=2.4 Hz, 1H).

3F 3-(2,2-Difluoro-ethyl)-1-(2'-(morpholin-4-ylmethyl)biphenyl-4-ylmethyl)imidazolidine-2,4-dione $^1$H-NMR (400 MHz, CDCl$_3$): δ 7.52 (m, 1H), 7.43 (m, 2H), 7.22-7.37 (m, 5H), 6.07 (t, t, J=4.3 Hz, 1H), 6.07 (t t, J=4.3 Hz, 1H), 3.90 (t d, J=4.6 Hz, 2H), 3.88 (s, 2H), 3.63 (t, J=4.6 Hz, 4H), 3.38 (s, 2H), 2.38 (t, J=4.3 Hz, 4H).

3G 3-(2-Fluoro-ethyl)-1-(2'-(morpholin-4-ylmethyl)biphenyl-4-ylmethyl)imidazolidine-2,4-dione $^1$H-NMR (400 MHz, CDCl$_3$): δ 7.51 (m, 1H), 7.42 (m, 2H), 7.22-7.37 (m, 5H), 4.63 (s, 2H), 4.63 (d t, J=4.1 Hz, 2H), 3.90 (d t, J=2.1 Hz, 2H), 3.84 (s, 2H), 3.64 (t, J=4.6 Hz, 4H), 3.39 (s, 2H), 2.38 (t, J=4.1 Hz, 4H).

3H 3-(2-Methoxy-ethyl)-1-(2'-(morpholin-4-ylmethyl)biphenyl-4-ylmethyl)imidazolidine-2,4-dione $^1$H-NMR (400 MHz, CDCl$_3$): δ 7.51 (m, 1H), 7.42 (m, 2H), 7.23-7.37 (m, 5H), 4.63 (s, 2H), 3.62 (d, J=5.4 Hz, 2H), 3.65 (t, J=4.9 Hz, 4H), 3.73 (t, J=5.9, 5.4 Hz, 2H), 3.82 (s, 2H), 3.39 (s, 3H), 3.38 (s, 2H), 2.38 (t, J=4.0 Hz, 4H).

3I 3-((2'-(Morpholin-4-ylmethyl)biphenyl-4-ylmethyl)-2,5-dioxo-imidazolidin-1yl)-acetic acid methyl ester $^1$H-NMR (400 MHz, CDCl$_3$): δ 7.51 (m, 1H), 7.43 (m, 2H), 7.21-7.39 (m, 5H), 4.66 (s, 2H), 4.32 (s, 2H), 3.90 (s, 2H), 3.79 (s, 3H), 3.66 (t, J=4.5 Hz, 4H), 3.38 (s, 2H), 2.38 (t, J=3.2 Hz, 4H).

3J 1-(2'-(Morpholin-4-ylmethyl)biphenyl-4-ylmethyl)-3-(2-oxo-butyl)imidazolidine-2,4-dione $^1$H-NMR (400 MHz, CDCl$_3$): δ 7.51 (m, 1H), 7.42 (m, 2H), 7.23-7.37 (m, 5H), 4.65 (s, 2H), 4.37 (5, 2H), 3.91 (s, 2H), 3.64 (t, J=4.4 Hz, 4H), 3.38 (s, 2H), 2.54 (m, 2H), 2.38 (t, J=4.5 Hz, 4H), 1.13 (t, J=7.4 Hz, 3H).

3K

3-Cyclopropylmethyl-1-(2'-(morpholin-4-ylmethyl)biphenyl-4-ylmethyl)imidazolidine-2,4-dione $^1$H-NMR (400 MHz, CDCl$_3$): δ 7.51 (dd, J=6.8 Hz, 1H), 7.43 (d, J=7.8 Hz, 2H), 7.28 (d, J=7.8 Hz, 2H), 7.22-7.36 (m, 3H), 4.63 (s, 2H), 3.82 (s, 2H), 3.64 (t, J=4.9 Hz, 4H), 3.42 (d, J=7.8 Hz, 2H), 3.37 (s, 2H), 2.36 (t, J=4.9 Hz, 4H), 1.21 (m, 1H), 0.52 (m, 2H), 0.38 (m, 2H).

EXAMPLE 4

1-(3'-(4,4-Difluoro-piperidin-1-ylmethyl)biphenyl-4-ylmethyl)imidazolidine-2,4-dione

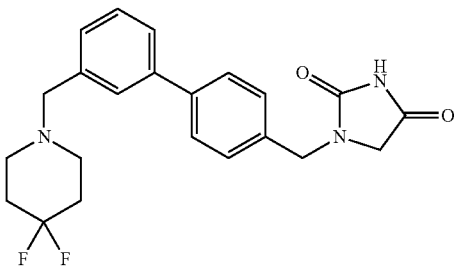

i)—To a solution of p-bromobenzyl bromide (10 g, 40 mmol) in THF (100 ml) and water (7.2 ml) were added glycine methyl ester hydrochloride (10 g, 80 mmol), potassium carbonate (22.1 g, 160 mmol) and tetrabutylammonium sulfate (136 mg, 0.4 mmol). After 1 h stirring at 40° C., the reaction mixture was poured in water and the product was extracted into ethyl acetate. The combined organic phases were washed with brine, dried over magnesium sulfate and concentrated under reduced pressure. Column chromatography afforded (4-bromo-benzylamino)acetic acid methyl ester (6.4 g) as a colorless oil.

ii)—To a solution of the product obtained in the previous step (2.8 g, 10.8 mmol) in dioxane/water (1:1, 60 ml) were added potassium isocyanate (1.32 g, 16.3 mmol) and acetic acid (1.98 ml, 34.6 mmol). After 1 h stirring at room temperature, the reaction mixture was concentrated under reduced pressure and water was added. The precipitate was collected and dried to give (1-(4-bromo-benzyl)ureido)acetic acid methyl ester (2.9 g) as a white powder.

iii)—To a solution of the product obtained in the previous step (2.8 g, 9.4 mmol) in dry methanol (50 ml) was added sodium methoxide (1.0 g, 18.9 mmol) under a nitrogen atmosphere. After stirring for 2 h at room temperature, the reaction mixture was concentrated under reduced pressure, water added and cooled to 0° C. The precipitate was collected and dried to give 1-(4-bromo-benzyl)imidazolidine-2,4-dione (3.7 g). The product was used in the following step without further purification.

iv)—A solution of the product obtained in the previous step (150 mg, 0.56 mmol) in 2-methoxyethanol/$H_2O$ (1/1: 100 ml), containing 3-formylphenylboronic acid (125 mg, 0.84 mmol), sodium hydrogen carbonate (94 mg, 1.12 mmol) and $(Ph_3P)_4Pd$ (32 mg, 0.028 mmol), was heated under reflux for 18 h under a nitrogen atmosphere. After cooling, the reaction mixture was filtered over dicalite and the product was extracted into ethyl acetate. The combined organic phases were washed with brine, dried over magnesium sulfate and concentrated under reduced pressure. Column chromatography afforded 4'-(2,4-Dioxo-imidazolidin-1-ylmethyl)biphenyl-3-carbaldehyde (365 mg).

v)—To a solution of the product obtained in the previous step (352 mg, 1.20 mmol) in dry methanol (10 ml), grinded molecular sieves (3 Å) and triethylamine (0.252 ml, 1.80 mmol) were added under a nitrogen atmosphere. After stirring for 15 minutes at room temperature, difluoropiperidine hydrochloride (377 mg, 2.39 mmol) was added portionwise. After stirring for 18 h at room temperature, sodium borohydride (excess) was added portionwise to the reaction mixture, while stirring vigorously. The thick slurry was filtered and the residue was thoroughly washed with methylene choride and methanol. The filtrate was concentrated under reduced pressure to obtain a brown solid substance which was extracted into ethyl acetate. The combined organic phases were washed with water, brine, dried over magnesium sulfate and concentrated under reduced pressure. Column chromatography afforded 1-(3'-(4,4-difluoro-piperidin-1-ylmethyl)biphenyl-4-ylmethyl)imidazolidine-2,4-dione (342 mg). $^1$H-NMR (400 MHz, $CDCl_3$): δ 7.60 (d, J=7.8 Hz, 2H), 7.53 (s, 1H), 7.48 (d, J=7.8 Hz, 1H), 7.41 (t, J=7.8 Hz, 1H), 7.34 (d, J=7.8 Hz, 2H), 7.32 (d, J=7.8 Hz, 1H), 4.58 (s, 2H), 3.84 (s, 2H), 3.61 (s, 2H), 2.48 (t, J=5.4 Hz, 4H), 2.00 (m, 4H).

EXAMPLE 5

Following a procedure analogous to that described in Example 2, step vii, using 1-(3'-(4,4-Difluoro-piperidin-1-ylmethyl)biphenyl-4-ylmethyl)imidazolidine-2,4-dione (Example 4, step v) as starting material, the following compounds were prepared:

5A

3-Allyl-1-(3'-(4,4-difluoro-piperidin-1-ylmethyl)biphenyl-4-ylmethyl)imidazolidine-2,4-dione (m/z)=440 $(M+H)^+$

5B

3-Cyclobutylmethyl-1-(3'-(4,4-difluoro-piperidin-1-ylmethyl)biphenyl-4-ylmethyl)imidazolidine-2,4-dione (m/z)=468 $(M+H)^+$

EXAMPLE 6

3-Cyclopropyl-1-(4'-fluoro-3'-(morpholin-4-ylmethyl)biphenyl-4-ylmethyl)imidazolidine-2,4-dione

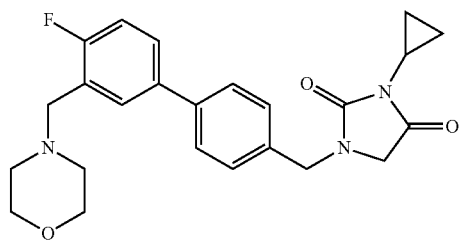

i)—To a solution of glycine (15 g, 200 mmol) in water (80 ml) were added an aqueous solution of sodium hydroxide (20 ml, 10 M) and a solution of 4-bromobenzaldehyde (37 g, 200 mmol) in methanol (440 ml). After 10 minutes stirring at room temperature sodium borohydride (7.5 g, 200 mmol) was added in portions to this suspension. After 18 h stirring at room temperature the reaction mixture was concentrated under reduced pressure and washed with diethyl ether. The aqueous phase was neutralized with concentrated hydrochloric acid. The precipitate was collected by filtration, washed with water and diethyl ether. Drying the white solid afforded 2-(4-bromobenzylamino)acetic acid (14.98 g). The product was used in the following step without purification.

ii)—To a suspension of the product obtained in the previous step (10 g, 41.0 mmol) in dichloromethane (100 ml) were added triethyl amine (17.1 ml, 123 mmol), cyclopropyl amine (4.26 ml, 61.5 mmol) and PyBOP (21.3 g, 41.0 mmol). After 18 h stirring at room temperature the reaction mixture was concentrated under reduced pressure. Column chromatography afforded 2-(4-bromo-benzylamino)-N-cyclopropyl-acetamide (9.3 g).

iii)—To a solution of the product obtained in the previous step (8 g, 28.3 mmol) in acetonitrile (200 ml) were added CDI (56.5 mmol, 9.16 g) and DMAP (6.90 g, 56.5 mmol). After 17 h stirring at 60° C. the reaction mixture was cooled and quenched by adding a saturated aqueous solution of sodium hydrogen carbonate. The product was extracted into ethyl acetate. The combined organic phases were dried over magnesium sulfate and concentrated under reduced pressure. Column chromatography afforded 1-(4-bromo-benzyl)-3-cyclopropyl-imidazolidine-2,4-dione (7.88 g).

iv)—To a solution of the product obtained in the previous step (0.5 g, 1.62 mmol) in toluene/ethanol (4/1; 25 ml) were added 4-fluoro-3-formylphenylboronic acid (0.41 g, 2.43 mmol), (Ph$_3$P)$_4$Pd (93.6 mg, 0.081 mmol) and potassium carbonate (6.3 ml 2M, 12.5 mmol). After 18 h stirring at 75° C. the reaction mixture was cooled and filtered over dicalite. The product was extracted into ethyl acetate. The combined organic phases were washed with water, brine, dried over magnesium sulfate and concentrated under reduced pressure. Column chromatography afforded 4'-(3-cyclopropyl-2,4-dioxo-imidazolidin-1-ylmethyl)-4-fluoro-biphenyl-3-carbaldehyde (0.28 g)

v)—Acetic acid (0.069 ml, 1.2 mmol) and sodium triacetoxyborohydride (847 mg, 4 mmol) were added to a solution of the product obtained in the previous step (0.28 g, 0.8 mmol) and morpholine (0.19 g, 2.27 mmol) in methanol (7.5 ml) at room temperature. After 18 h stirring the reaction mixture was quenched by the addition of water and the product was extracted into dichloromethane. The combined organic layers were washed with a aqueous solution of citric acid (3%), water, dried over magnesium sulfate and concentrated under reduced pressure. Column chromatography afforded 3-cyclopropyl-1-(4'-fluoro-3'-(morpholin-4-ylmethyl)biphenyl-4-ylmethyl)imidazolidine-2,4-dione (76 mg). $^1$H NMR (DMSO): δ 7.65 (m, 1H), 7.62 (d, J=5.42 Hz, 2H), 7.58 (m, 1H), 7.55 (d, J=5.42 Hz, 2H), 7.26 (t, J=5.42 Hz, 1H), 4.50 (s, 2H), 3.82 (s, 2H), 3.56 (m, 4H), 2.55 (m, 1H), 2.41 (br s, 4H), 0.83 (d, J=4.51 Hz, 4H).

EXAMPLE 7

Following procedures analogous to that described in Example 6, using glycine and aminomethylcyclopropane as starting material, the following compounds were prepared.

7A 1-(4'-(3-Cyclopropylmethyl-2,4-dioxo-imidazolidin-1-ylmethyl)biphenyl-2-yl-methyl)piperidine-4-carbonitrile $^1$H NMR (400 MHz, CDCl$_3$): δ 7.48 (d, J=7.39 Hz, 1H), 7.32 (m, 6H), 7.22 (d, J=7.39 Hz, 1H), 4.63 (s, 2H), 3.82 (s, 2H), 3.42 (d, J=7.83 Hz, 2H), 3.36 (s, 2H), 2.57 (bs, 3H), 2.21 (bs, 2H), 1.82 (m, 4H), 1.2 (m, 1H), 0.52 (m, 2H), 0.37 (m, 2H).

7B

3-Cyclopropylmethyl-1-(2'-(piperidin-1-ylmethyl) biphenyl-4-ylmethyl)imidazolidine-2,4-dione $^1$H NMR (400 MHz, CDCl$_3$): δ 7.53 (d, J=7.81 Hz, 1H), 7.41 (d, J=8.68 Hz, 2H), 7.31 (m, 4H), 7.21 (d, J=7.81 Hz, 1H), 4.62 (s, 2H), 3.81 (s, 2H), 3.42 (d, J=8.24 Hz, 2H), 3.32 (s, 2H), 2.27 (bs, 4H), 1.50 (m, 4H), 1.38 (bs, 2H), 1.21 (m, 1H), 0.52 (q, 2H), 0.38 (q, 2H).

Following procedures analogous to that described in Example 6, using glycine and cyclopropyl amine as starting material, the following compounds were prepared.

7C

3-Cyclopropyl-1-(3'-(thiomorpholin-4-ylmethyl) biphenyl-4-ylmethyl)imidazolidine-2,4-dione $^1$H NMR (400 MHz, CDCl$_3$): δ 7.58 (d, J=8.70 Hz, 2H), 7.51 (t, 1H), δ 7.46 (m, 1H), δ 7.39 (t, J=8.70 Hz, 1H), δ 7.32 (d, J=8.70, 2H), δ 4.58 (s, 2H), δ3.71 (s, 2H), δ 3.58 (s, 2H), 2.75 (m, 8H), δ 2.65 (m, 1H), δ 1.00 (s, 4H).

7D

3-Cyclopropyl-1-(3'-(1,1-dioxo-1λ$^6$-thiomorpholin-4-ylmethyl)biphenyl-4-ylmethyl)imidazolidine-2,4-dione $^1$H NMR (400 MHz, CDCl$_3$): 7.57(d, J=9.24 Hz, 2H), 7.5 (m, 2H), 7.42 (t, J=6.93 Hz, 1H), 7.33 (d, J=9.24 Hz, 2H), 7.30 (m 1H), 4.59 (s, 2H), 3.72 (s, 2H), 3.74 (s, 2H), 3.05 (m, 8H), 2.62 (m 1H), 0.98 (m, 4H)

Following procedures analogous to that described in Example 6, using glycine and isobutyl amine as starting material, the following compounds were prepared.

7E

3-Isobutyl-1-(3'-(piperidin-1-ylmethyl)biphenyl-4-ylmethyl)imidazolidine-2,4-dione $^1$H NMR (400 MHz, CDCl$_3$): δ 7.60 (d, J=8.88 Hz, 2H), 7.53 (s, 1H), 7.45 (m, 1H), 7.38 (t, J=8 Hz, 1H), 7.12 (d, J=8.88 Hz, 2H), 4.6 (s, 2H), 3.77 (s, 2H), 3.55 (s, 2H), 3.36 (d, J=7.95 Hz, 2H), 2.4 (bs, 4H), 2.10 (m, 1H), 1.42 (bs, 4H), 1.26 (bs, 2H), 0.94 (d, J=6.6 Hz, 6H)

7F 1-(4'-Fluoro-3'-(morpholin-4-ylmethyl)biphenyl-4-ylmethyl)-3-isobutyl-imidazolidine-2,4-dione $^1$H NMR (400 MHz, CDCl$_3$): δ 7.58 (m, 1H), 7.56 (d, J=9.52 Hz, 2H), 7.43 (m, 1H), 7.32 (d, J=9.52 Hz, 2H), 7.11 (t, J=8.57 Hz, 1H), 4.6 (s, 2H), 3.77 (s, 2H), 3.63 (2H, s), 3.52

(t, J=4.73 Hz, 4H), 3.37 (d, J=7.1 Hz, 2H), 2.52 (t, J=4.73 Hz, 4H), 2.10 (m, 1H), 0.94 (d, J=7.1 Hz, 6H).

7G 1-(2'-Fluoro-5'-(morpholin-4-ylmethyl)biphenyl-4-ylmethyl)-3-isobutyl-imidazolidine-2,4-dione $^1$H NMR (400 MHz, CDCl$_3$): δ 7.55 (d, J=8.83 Hz, 2H), 7.37 (d, J=6.62 Hz, 1H), 7.33 (d, J=8.83 Hz, 2H), 7.28 (m, 1H), 7.1 (m, 1H), 4.62 (s, 2H), 3.79 (s, 2H), 3.72 (t, J=4.85 Hz, 4H), 3.5 (s, 2H), 3.36 (d, J=7.94 Hz, 2H), 2.45 (br s, 4H), 2.10 (m, 1H), 0.93 (d, J=7.94 Hz, 6H)

7H 1-(2'-Fluoro-3'-(morpholin-4-ylmethyl)biphenyl-4-ylmethyl)-3-isobutyl-imidazolidine-2,4-dione $^1$H NMR (400 MHz, CDCl$_3$): δ 7.53 (d, J=8.86 Hz, 2H), 7.38 (t, J=6.65 Hz, 1H), 7.33 (d, J=8.86 Hz, 2H), 7.36-7.28 (m, 1H), 7.18 (t, J=7.5 Hz, 1H), 4.60 (s, 2H), 3.80 (s, 2H), 3.72 (t, J=4.43 Hz, 4H), 3.53 (s, 2H), 3.38 (d, J=8.42 Hz, 2H), 2.53 (t, J=4.43 Hz, 4H), 2.10 (m, 1H), 0.93 (d, J=7.97 Hz, 6H)

EXAMPLE 8

3-Cyclobutylmethyl-1-(3'-(piperidin-1-ylmethyl)biphenyl-4-ylmethyl)imidazolidine-2,4-dione i)—To a solution of 1-(4-bromo-benzyl)imidazolidine-2,4-dione (Example 4, step iii) (5.91 g, 21.96 mmol) in DMF (50 ml) were added (bromomethyl)cyclobutane (6.55 g, 43.9 mmol) and potassium carbonate (9.11 g, 65.9 mmol) under a nitrogen atmosphere. After stirring for 20 h at room temperature, the reaction mixture was concentrated under reduced pressure. The product was extracted in ethyl acetate and the combined organic layers were washed with water, brine, dried over sodium sulfate and concentrated under reduced pressure to give 1-(4-bromo-benzyl)-3-cyclobutylmethyl-imidazolidine-2,4-dione (5.30 g).

ii)—Following a procedure analogous to that described in Example 6, step iv, the product obtained in the previous step (2.5 g), was converted to 4'-(3-cyclobutylmethyl-2,4-dioxo-imidazolidin-1-ylmethyl)biphenyl-3-carbaldehyde (1.10 g).

iii)—Following a procedure analogous to that described in Example 6, step v, the product obtained in the previous step (1.1 g), was converted to 3-cyclobutylmethyl-1-(3'-(piperidin-1-ylmethyl)biphenyl-4-ylmethyl)imidazolidine-2,4-dione (337 mg).

$^1$H NMR (400 MHz, CDCl3): δ 7.95 (s, 1H), 7.70 (d, J=8.7 Hz, 2H), 7.60 (d, J=7.4 Hz, 1H), 7.53 (t, J=7.8 Hz, 1H), 7.35 (d, J=7.8 Hz, 2H), 4.6 (s, 2H), 3.75 (s, 2H), 3.58 (d, J=7.4 Hz, 2H), 3.48 (d, J=11.4 Hz, 2H), 2.72 (m, 1H), 2.60 (q, 2H), 2.38 (q, 2H), 2.05 (m, 2H), 1.85 (m, 6H), 1.35 (m, 1H).

EXAMPLE 9

Following procedures analogous to that described in Example 8, the following compounds were prepared.

9A 3-(2,2-Difluoro-ethyl)-1-(3'-(piperidin-1-ylmethyl)biphenyl-4-ylmethyl)imidazolidine-2,4-dione $^1$H NMR (400 MHz, CDCl3): δ 8.01 (s, 1H), 7.68 (m, J=8.2 Hz, 3H), 7.58 (d, J=7.4 Hz, 1H), 7.51 (m, 1H), 7.37 (d, J=8.2 Hz, 2H), 6.20-5.90 (m, 1H), 4.62 (s, 2H), 4.18 (d, J=5.6 Hz, 2H), 3.93 (m, 2H), 3.84 (s, 2H), 3.48 (d, J=10.5 Hz, 2H), 2.61 (m, 2H), 2.35 (m, 2H), 1.95 (m, 3H), 1.38 (m, 1H).

9B 1-(4'-Fluoro-3'-(piperidin-1-ylmethyl)biphenyl-4-ylmethyl)-3-isobutyl-imidazolidine-2,4-dione $^1$H NMR (400 MHz, CDCl3): δ 7.00 (t, J=7.7 Hz, 1H), 7.53 (m, 3H), 7.36 (m, 3H), 4.62 (s, 2H), 4.25 (s, 2H), 3.79 (s, 2H), 3.50 (s, 2H), 3.37 (d, J=7.0 Hz, 2H), 2.65 (s, 2H), 2.35 (s, 2H), 2.10 (m, 1H), 1.86 (s, 3H), 1.37 (s, 1H), 0.94 (d, J=7.0 Hz, 6H).

EXAMPLE 10

3-(2,2-Difluoro-ethyl)-1-(2'-fluoro-3'-(piperidin-1-ylmethyl)biphenyl-4-ylmethyl)imidazolidine-2,4-dione i)—Following a procedure analogous to that described in Example 6, step v, piperidine (0.88 ml, 8.93 mmol) and 2-fluoro-3-formylphenylboronic acid (500 mg, 2.98 mmol) were converted to 2-fluoro-3-(piperidin-1-ylmethyl)phenyl-boronic acid (210 mg).

ii)—Following a procedure analogous to that described in Example 8, step i, 1-(4-bromobenzyl)imidazolidine-2,4-dione (Example 4, step iii) was converted to 1-(4-bromobenzyl)-3-(2,2-difluoro-ethyl)imidazolidine-2,4-dione.

iii)—Following a procedure analogous to that described in Example 6, step iv, the products obtained in the previous steps were converted to 3-(2,2-difluoro-ethyl)-1-(2'-fluoro-3'-(piperidin-1-ylmethyl)biphenyl-4-ylmethyl)imidazolidine-2,4-dione.

$^1$H NMR (400 MHz, CDCl$_3$): δ 7.49 (d, J=8.15 Hz, 2H), 7.33 (t, J=7.40 Hz, 1H), 7.25 (d, J=8.06 Hz, 2H), 7.22 (d, J=7.40 Hz, 1H) 7.11 (t, J=7.62 Hz, 1H), 5.84-6.13 (tt, J$_{HF}$=55.85 Hz, J$_{HH}$=4.52, 1H) 4.55 (s, 2H), 3.85 (dt, J$_{HF}$=13.87 Hz, J$_{HH}$=4.62 Hz, 2H), 3.79 (s, 2H), 3.55 (s, 2H), 2.39 (bs, 4H), 1.54 (m, 4H), 1.37 (bs, 2H)

EXAMPLE 11

Following procedures analogous to that described in Example 10, the following compounds were prepared.

11A 1-(2'-Fluoro-3'-(piperidin-1-ylmethyl)biphenyl-4-ylmethyl)-3-isobutyl-imidazolidine-2,4-dione $^1$H NMR (400 MHz, CDCl$_3$): δ 7.48 (d, J=8.12 Hz, 2H), 7.34 (t, J=7.16 Hz, 1H) 7.25 (d, J=8.12 Hz, 3H), 7.12 (t, J=7.66 Hz, 1H), 4.55 (s, 2H), 3.72 (s, 2H), 3.63 (bs, 2H), 3.30 (d, J=7.44, 2H), 2.45 (bs, 4H), 2.04 (m, 1H), 1.57 (m, 4H), 1.38 (bs, 2H), 0.87 (d, J=6.33 Hz, 6H)

11B 1-(3'-(1,1-Dioxo-1λ$^6$-thiomorpholin-4-ylmethyl)-4'-fluoro-biphenyl-4-ylmethyl)-3-isobutyl-imidazolidine-2,4-dione $^1$H NMR (400 MHz, CDCl$_3$): δ 7.79 (bs, 1H), 7.57 (dd, J=7.43 and 7.04 Hz, 1H), 7.52 (d, J=7.04 Hz, 2H), 7.42-7.34

(m, 3H), 4.63 (s, 2H), 4.33 (s, 2H), 3.80 (s, 2H), 3.69-3.56 (bs, 4H), 3.37 (d, J=7.43, 2H), 2.18-2.03 (m, 1H), 0.94 (d, J=7.04 Hz, 6H).

11C

3-Cyclopropylmethyl-1-(3'-(1,1-dioxo-1$\lambda^6$-thiomorpholin-4-ylmethyl)biphenyl-4-ylmethyl)imidazolidine-2,4-dione $^1$H NMR (400 MHz, CDCl$_3$): δ 7.94 (s, 1H), 7.72-7.68 (m, 1H), 7.66 (d, J=8.21 Hz, 2H), 7.54 (d, J=5.87 Hz, 2Hz), 7.37 (d, J=8.21 Hz, 2H), 4.62 (s, 2H), 4.27 (s, 2H), 3.78 (s, 2H), 3.67-3.54 (m, 4H), 3.42 (d, J=7.43, 2H), 1.24-1.14 (m, 1H), 0.56-0.48 (m, 2H), 0.40-0.34 (m, 2H).

11D

3-Cyclopropylmethyl-1-(3'-(1,1-dioxo-1$\lambda^6$-thiomorpholin-4-ylmethyl)-4'-fluoro-biphenyl-4-ylmethyl)imidazolidine-2,4-dione $^1$H NMR (400 MHz, CDCl$_3$): δ 7.83-7.73 (m, 1H), 7.62-7.48 (m, 3H), 7.41-7.35 (m, 3H), 4.64 (s, 2H), 4.35 (s, 2H), 3.81 (s, 2H), 3.64 (bs, 4H), 3.41 (d, J=7.04, 2H), 1.25-1.14 (m, 1H), 0.56-0.48 (m, 2H), 0.41-0.33 (m, 2H).

11E 1-(3'-(1,1-Dioxo-1$\lambda^6$-thiomorpholin-4-ylmethyl)biphenyl-4-ylmethyl)-3-isobutyl-imidazolidine-2,4-dione $^1$H NMR (400 MHz, CDCl$_3$): δ 7.88 (s, 1H), 7.64 (d, J=7.04 Hz, 1H), 7.65 (d, J=8.22 Hz, 2H), 7.57-7.50 (m, 2H), 7.36 (d, J=8.22 Hz, 2H), 4.62 (s, 2H), 4.24 (s, 2H), 3.78 (s, 2H), 3.59 (bs, 4H), 3.37 (d, J=7.43, 2H), 2.16-2.04 (m, 1H), 0.94 (d, J=6.65 Hz, 6H).

EXAMPLE 12

3-Cyclobutyl-1-((4'-fluoro-3'-(thiomorpholinomethyl)biphenyl-4-yl)methyl)imidazolidine-2,4-dione i)—Following a procedure analogous to that described in Example 6 step v, thiomorpholine and 4-fluoro-3-formylphenylboronic acid were converted to 4-fluoro-3-(thiomorpholino-1-ylmethyl)phenylboronic acid ii)—1-(4-bromobenzyl)-3-cyclobutyl-imidazolidine-2,4-dione was prepared following a procedure analogous to that described in Example 6, step i to iii.

iii)—Following a procedure analogous to that described in Example 6, step iv, the products obtained in the previous steps were converted to 3-cyclobutyl-1-((4'-fluoro-3'-(thiomorpholinomethyl)biphenyl-4-yl)methyl)imidazolidine-2,4-dione.

$^1$H NMR (400 MHz, CDCl$_3$): δ 7.53 (dd, J=8.22 and 1.57 Hz, 2H), 7.39-7.28 (m, 4H), 7.18 (dd, J=7.83 and 7.43 Hz, 1H), 4.64-4.52 (m, 3H), 3.71 (s, 2H), 3.66 (s, 2H), 2.96-2.83 (m, 2H), 2.81-2.66 (m, 8H), 2.33-2.13 (m, 2H), 1.93-1.68 (m, 2H).

EXAMPLE 13

Following procedures analogous to that described in Example 12, the following compounds were prepared.

13A

3-Cyclobutyl-1-(3'-(1,1-dioxo-1$\lambda^6$-thiomorpholin-4-ylmethyl)biphenyl-4-ylmethyl)imidazolidine-2,4-dione $^1$H NMR (400 MHz, CDCl$_3$): δ 7.90 (bs, 1H), 7.72-7.67 (m, 1H), 7.65 (d, J=8.60 Hz, 2H), 7.58-7.51 (m, 2H), 7.36 (d, J=8.21 Hz, 2H), 4.64-4.53 (m, 3H), 4.22 (bs, 2H), 3.71 (s, 2H), 3.62-3.51 (bs, 8H), 2.96-2.84 (m, 2H), 2.25-2.15 (m, 2H), 1.92-1.68 (m, 2H).

13B

3-Cyclobutyl-1-(3'-(1,1-dioxo-1$\lambda^6$-thiomorpholin-4-ylmethyl)-4'-fluoro-biphenyl-4-ylmethyl)imidazolidine-2,4-dione $^1$H NMR (400 MHz, CDCl$_3$): δ 7.57 (bs, 1H), 7.60-7.48 (m, 3H), 7.41-7.33 (m, 3H), 4.65-4.54 (m, 3H), 4.30 (bs, 2H), 3.71 (m, 2H), 3.65-3.52 (m, 8H), 2.96-2.81 (m, 2H), 2.24-2.14 (m, 2H), 1.93-1.66 (m, 2H).

13C

3-Cyclopropyl-1-(3'-(1,1-dioxo-1$\lambda^6$-thiomorpholin-4-ylmethyl)biphenyl-4-ylmethyl)imidazolidine-2,4-dione $^1$H NMR (400 MHz, CDCl$_3$): δ 7.78-7.68 (bs, 1H), 7.58-7.48 (m, 3H), 7.41-7.35 (m, 4H), 4.60 (s, 2H), 4.33 (bs, 2H), 3.73 (s, 2H), 3.70-3.47 (m, 8H), 2.66-2.59 (m, 1H), 1.03-0.94 (m, 4H).

EXAMPLE 14

1-(3'-Fluoro-5'-(piperidin-1-ylmethyl)biphenyl-4-ylmethyl)-3-isobutyl-imidazolidine-2,4-dione i)—To a solution of 1-(4-bromobenzyl)-3-isobutyl-imidazolidine-2,4-dione (3 g, 9.22 mmol) in DMF (50 ml), bis(pinacolato)diboron (2.8 g, 11.07 mmol) and potassium acetate (2.72 g, 27.7 mmol) were added under a nitrogen atmosphere. After stirring for 2 minutes at room temperature (PPh$_2$)$_2$ferrocene Pd(II)Cl (0.224 g, 0.277 mmol) was added. After stirring 17 h at 75° C. the reaction mixture was cooled to room temperature and quenched by addition of water and the product was extracted into ethyl acetate.

The combined organic layers were washed with a saturated aqueous solution of sodium hydrogen carbonate, brine, dried over sodium sulfate and concentrated under reduced pressure to give 3-isobutyl-1-(4-(4,4,5,5-tetramethyl-(1,3,2)dioxaborolan-2-yl)-benzyl)imidazolidine-2,4-dione (6.36 g) as a crude product.

ii)—Following a procedure analogous to that described in Example 6, step iv, the product obtained in the previous step (0.253 g), was converted to 1-(3'-fluoro-5'-(piperidin-1-ylmethyl)biphenyl-4-ylmethyl)-3-isobutyl-imidazolidine-2,4-dione.

$^1$H NMR (400 MHz, CDCl$_3$): δ 7.57 (d, J=8.01 Hz, 2H), 7.32 (d, J=8.01 Hz, 2H), 7.30 (s, 1H), 7.14 (t, J=9.35 Hz, 1H), 7.06 (t, J=9.35 Hz, 1H), 4.61 (s, 2H), 3.77 (s, 2H), 3.50 (s,

2H), 3.37 (d, J=6.33, 2H), 2.40 (bs, 4H), 2.10 (m, 1H), 1.60 (bs, 4H), 1.44 (m, 2H), 0.93 (d, J=6.33 Hz, 6H).

EXAMPLE 15

(S)-3-(cyclopropylmethyl)-1-((4'-fluoro-3'-((tetrahydrofuran-3-ylamino)methyl)biphenyl-4-yl)methyl)imidazolidine-2,4-dione i)—Following a procedure analogous to that described in Example 6 step v, (S)-tetrahydrofuran-3-amine hydrochloride and 5-bromo-2-fluorobenzaldehyde were converted to (S)—N-(5-bromo-2-fluorobenzyl)tetrahydrofuran-3-amine.

ii)—3-(cyclopropylmethyl)-1-(4-(4,4,5,5-tetramethyl-1,3,2-dioxaborolan-2-yl)benzyl)imidazolidine-2,4-dione was prepared following a procedure analogous to that described in Example 14, step i.

iii)—Following a procedure analogous to that described in Example 6, step iv, the products obtained in the previous steps were converted to (S)-3-(cyclopropylmethyl)-1-((4'-fluoro-3-((tetrahydrofuran-3-ylamino)methyl)biphenyl-4-yl)methyl)imidazolidine-2,4-dione hydrochloride $^1$H NMR (400 MHz, DMSO): δ 7.96 (m, 1H), 7.81-7.73 (m, 1H), 7.69 (d, J=8.22 Hz, 2H), 7.44-7.33 (m, 3H), 4.56 (s, 2H) 4.25 (bs, 2H), 3.99-3.87 (m, 5H), 3.84-3.75 (m, 1H), 3.71-3.61 (m, 1H), 3.27 (d, J=7.04 Hz, 2H), 2.31-2.19 (m, 1H), 2.10-1.96 (m, 1H), 1.11-0.99 (m, 14H), 0.49-0.42 (m, 2H), 0.32-0.25 (m, 2H).

EXAMPLE 16

Following procedures analogous to that described in Example 15, the following compounds were prepared.

16A (R)-3-(cyclopropylmethyl)-1-((4'-fluoro-3'-((tetrahydrofuran-3-ylamino)methyl)biphenyl-4-yl)methyl)imidazolidine-2,4-dione $^1$H NMR (400 MHz, CDCl$_3$): δ 8.10 (m, 1H), 7.65 (d, J=8.22 Hz, 2H), 7.61-7.54 (m, 1H), 7.30 (d, J=8.22 Hz, 2H), 7.16 (dd, J=9.00 and 8.61 Hz, 1H), 4.58 (s, 2H) 4.22-4.08 (m, 4H), 3.90-3.82 (m, 1H), 3.80-3.71 (m, 3H), 3.66-3.57 (m, 1H), 3.42 (d, J=7.04 Hz, 2H), 2.38-2.14 (m, 2H), 1.25-1.14 (m, 1H), 0.56-0.48 (m, 2H), 0.41-0.34 (m, 2H).

16B 3-(cyclopropylmethyl)-1-((4'-fluoro-3'-((tetrahydro-2H-pyran-4-ylamino)methyl)biphenyl-4-yl)methyl)imidazolidine-2,4-dione $^1$H NMR (400 MHz, DMSO): δ 8.07 (m, 1H), 7.78 (m, 1H), 7.71 (d, J=7.83 Hz, 2H), 7.41 (m, 3H), 4.56 (s, 2H) 4.27 (bs, 2H), 3.95 (m, 4H), 3.46-3.23 (m, 5H), 2.11-1.97 (m, 2H), 1.76-1.58 (m, 2H), 1.14-0.99 (m, 1H), 0.50-0.39 (m, 2H), 0.31-0.25 (m, 2H).

16C 1-((3'-((tetrahydro-2H-pyran-4-ylamino)methyl)biphenyl-4-ylmethyl)-3-(2,2,2-trifluoroethyl)imidazolidine-2,4-dione $^1$H NMR (400 MHz, DMSO): δ 7.93 (s, 1H), 7.76-6.96 (m, 3H), 7.56-7.51 (m, 2H), 7.43 (d, J=8.22 Hz, 2H), 4.59 (s, 2H) 4.29-4.20 (m, 4H), 4.08 (s, 2H), 3.97-3.90 (m, 2H), 3.37-3.27 (m, 3H), 2.09-2.00 (m, 2H), 1.74-1.58 (m, 2H).

16D (R)-1-((4'-fluoro-3'-((tetrahydrofuran-3-ylamino)methyl)biphenyl-4-yl)methyl)-3-(2,2,2-trifluoroethyl)imidazolidine-2,4-dione $^1$H NMR (400 MHz, DMSO): δ 8.00 (m, 1H), 7.83-7.74 (m, 1H), 7.70 (d, J=8.22 Hz, 2H), 7.46-7.37 (m, 3H), 4.58 (s, 2H) 4.32-4.20 (m, 4H), 4.07 (s, 2H), 3.99-3.87 (m, 3H), 3.86-3.76 (m, 2H), 3.71-3.62 (m, 2H), 3.32-3.20 (m, 1H), 2.12-1.98 (m, 1H).

16E (S)-1-((4'-fluoro-3'-((tetrahydrofuran-3-ylamino)methyl)biphenyl-4-yl)methyl)-3-(2,2,2-trifluoroethyl)imidazolidine-2,4-dione $^1$H NMR (400 MHz, DMSO): δ 8.04-8.00 (m, 1H), 7.83-7.76 (m, 1H), 7.71 (d, J=8.22 Hz, 2H), 7.46-7.37 (m, 3H), 4.58 (s, 2H), 4.31-4.20 (m, 3H), 4.07 (s, 2H), 3.99-3.88 (m, 3H), 3.85-3.78 (m, 1H), 3.67 (dd, J=8.22 Hz, 1H), 2.35-2.21 (m, 1H), 2.12-2.02 (m, 1H).

16F (R)-1-((4'-fluoro-3'-((tetrahydrofuran-3-ylamino)methyl)biphenyl-4-yl)methyl)-3-isopropylimidazolidine-2,4-dione $^1$H NMR (400 MHz, DMSO): δ 8.07-8.00 (m, 1H), 7.81-7.75 (m, 1H), 7.70 (d, J=8.22 Hz, 2H), 7.43-7.36 (m, 3H), 4.52 (s, 2H), 4.30-4.15 (m, 3H), 3.99-3.90 (m, 3H), 3.89-3.78 (m, 3H), 3.68 (dd, J=8.22 and 7.83 Hz, 1H), 2.33-2.21 (m, 1H), 2.14-2.03 (m, 1H), 1.34 (d, J=7.04 Hz, 6H).

16G 1-((4'-fluoro-3'-((tetrahydro-2H-pyran-4-ylamino)methyl)biphenyl-4-yl)methyl)-3-isopropylimidazolidine-2,4-dione $^1$H NMR (400 MHz, DMSO): δ 8.01 (m, 1H), 7.82-7.74 (m, 1H), 7.70 (d, J=8.22 Hz, 2H), 7.46-7.37 (m, 3H), 4.52 (s, 2H), 4.33-4.16 (m, 3H), 4.00-3.91 (m, 2H), 3.86 (s, 2H), 3.48-3.27 (m, 3H), 2.09-2.00 (m, 2H), 1.72-1.59 (m, 2H), 1.34 (d, J=6.65 Hz, 6H).

16H 1-((4'-fluoro-3'-((tetrahydro-2H-pyran-4-ylamino)methyl)biphenyl-4-yl)methyl)-3-(2,2,2-trifluoroethyl)imidazolidine-2,4-dione $^1$H NMR (400 MHz, DMSO): δ 8.08-8.02 (m, 1H), 7.82-7.75 (m, 1H), 7.72 (d, J=8.22 Hz, 2H), 7.46-7.37 (m, 3H), 4.58 (s, 2H) 4.32-4.20 (m, 4H), 4.07 (s, 2H), 3.98-3.91 (m, 2H), 3.46-3.27 (m, 3H), 2.10-2.00 (m, 2H), 1.74-1.59 (m, 2H).

16I (S)-1-((4'-fluoro-3'-((tetrahydrofuran-3-ylamino) methyl)biphenyl-4-yl)methyl)-3-isopropylimidazolidine-2,4-dione $^1$H NMR (400 MHz, DMSO): δ 8.00 (m, 1H), 7.82-7.75 (m, 1H), 7.70 (d, J=8.22 Hz, 2H), 7.45-7.37 (m, 3H), 4.52 (s, 2H), 4.31-4.15 (m, 3H), 3.98-3.88 (m, 3H), 3.87-3.78 (m, 3H), 3.67 (dd, J=8.22 and 7.83 Hz, 1H), 2.35-2.22 (m, 1H), 2.12-2.01 (m, 1H), 1.34 (d, J=7.04 Hz, 6H).

EXAMPLE 17

Agonist-induced cAMP Change in Human CB2 Tranfected CHO Cells

Adenylate cyclase assays were carried out using CHO cells stably over-expressing the human recombinant $CB_2$ receptor. Cells were cultured in DMEM/HAMF12 containing 1% (v/v) penicillin/streptomycin (Gibco 15140-122), 10% FBS Biowitthaker (DE-14-701-F) and 400 μg/ml Geneticin (Invitrogen 10131-027). Compounds and reference (CP55,940) were dissolved in DMSO and dilutions were made in serum free medium containing 10 μM Rolipram (Sigma R6520) and 2 μM Forskolin (Sigma, F3917). 10 μl of each dilution was transferred to an assay plate (384-well white culture plate, Perkin Elmer). Cell suspensions containing $10^6$ cells/ml in DMEM/HAMF12 containing 1% (v/v) penicillin/streptomycin were prepared from hCB2_C2-CHO cells and 10 μl (10,000 cells/well) thereof was transferred to the assay plate and cells were incubated for 45 min at 37° C. Homogeneous time-resolved fluorescence (HTRF; CisBio) was used as a read-out by sequentially adding 10 μl cAMP-XL665 and 10 μl anti-cAMP(Eu) cryptate; after 1 h incubation at room temperature, fluorescence at 615 nm and 665 nm was measured on Envision (Perkin Elmer). Results were calculated from the 665 nm/615 nm ratios obtained for individual compounds and were compared to values obtained for the reference compound. The compounds from Example 2-16 have an $EC_{50} < 4 \times 10^{-7}$ M for CB2.

EXAMPLE 17A

Agonist-induced cAMP Change in Human CB1 Tranfected CHO Cells

Adenylate cyclase assays were carried out using CHO cells stably over-expressing the human recombinant $CB_1$ receptor. Cells were cultured in DMEM/HAMF12 containing 1% (v/v) penicillin/streptomycin (Gibco 15140-122), 10% FBS Biowitthaker (DE-14-701-F), 400 μg/ml Geneticin (Invitrogen 10131-027) and Zeocine 250 μg/ml (Invitrogen, 45-0430). Compounds and reference (CP55,940) were dissolved in DMSO and dilutions were made in serum free medium containing 10 μM Rolipram (Sigma R6520) and 2 μM Forskolin (Sigma, F3917). 10 μl of each dilution was transferred to an assay plate (384-well white culture plate, Perkin Elmer). Cell suspensions containing $10^6$ cells/ml in DMEM/HAMF12 containing 1% (v/v) penicillin/streptomycin were prepared from hCB$_1$_A2-CHO cells and 10 μl (10,000 cells/well) thereof was transferred to the assay plate and cells were incubated for 45 min at 37° C.

Homogeneous time-resolved fluorescence (HTRF; CisBio) was used as a read-out by sequentially adding 10 μl cAMP-XL665 and 10 μl anti-cAMP(Eu) cryptate; after 1 h incubation at room temperature, fluorescence at 615 nm and 665 nm was measured on Envision (Perkin Elmer). Results were calculated from the 665 nm/615 nm ratios obtained for individual compounds and were compared to values obtained for the reference compound. The compounds from Example 2-16 have an $EC_{50} > 10^{-6}$ M for CB1.

EXAMPLE 18

The Rat (Chung) Model of Neuropathic Pain

In this model, mechanical allodynia is induced by tight ligation of the left L5 spinal nerve. This assay has been employed successfully to demonstrate anti-allodynic effects of anticonvulsants (gabapentin), antidepressants (duloxetine) and opioid analgesics (morphine) which are used clinically in the treatment of neuropathic pain.

Male Wistar rats (228-301 g body weight at time of surgery) were employed in the study. Rats were placed on an elevated (~40 cm) mesh floor in perspex boxes and the rats' withdrawal threshold to a mechanical stimulus (calibrated von Frey filaments) was measured using filaments of increasing force (2.6-167 mN). The von Frey filaments were applied to the plantar surface of the paw and threshold response determined using the up and down method. A positive response was noted if the paw was sharply withdrawn. A cut-off of 15 g was selected as the upper limit for testing. Following baseline measurements each animal was anaesthetised and the L5 spinal nerve tightly ligated. The animals were allowed to recover from the surgery for a period of at least three days. On the day of drug administration the paw withdrawal thresholds were re-measured (0 min). Immediately after this reading, the rats were dosed orally with vehicle or test compound and readings measured at various time points after compound administration.

Data were expressed as mean±s.e.m. Statistical analysis was performed using the Kruskal-Wallis one-way analysis of variance, a non-parametric statistical test. Each of the treatment groups were then compared against the vehicle group, using the non-parametric Dunn's test.

Oral administration of the selective CB2 receptor agonist of Example 3K (4.5-45 μmol/kg p.o.) attenuated mechanical allodynia in a dose-dependent fashion (Table 1; FIG. 1) at 120 and 180 min post drug administration, respectively. The Minimum effective dose (MED) was 15 μmol/kg p.o. for Example 3K.

These data demonstrate that selective CB2 receptor agonist posses potent oral anti-allodynic activity in a rat model of neuropathic pain.

TABLE 1

Effect of compound 3K on mechanical allodynia induced by spinal nerve ligation in rats.

| Compound | Route | Dose (μmol/kg) | Number of animals tested | Withdrawal threshold (g) at peak effect |
|---|---|---|---|---|
| Vehicle | p.o. | 2 ml·kg$^{-1}$ | 7 | 2.7 ± 0.2 |
| 3K | p.o. | 4.5 | 8 | 5.8 ± 1.1 |
| 3K | p.o. | 15 | 8 | 6.4 ± 1.0* |
| 3K | p.o. | 45 | 8 | 7.4 ± 1.3* |

Dose groups and number of animals per group.
*p ≦ 0.05, Dunns test comparing vehicle-treated and compound-treated animals.

EXAMPLE 19

Mechanical Hyperalgesia in the Rat

In this rat model of inflammatory pain, inflammation is induced by subcutaneous injection of complete Freund's adjuvant (CFA) into the hind paw. The associated mechanical hyperalgesia is quantified by measuring the reduction in paw withdrawal threshold (PWT) to a mechanical compression of the paw. This assay has been employed successfully to demonstrate anti-hyperalgesic effects of non-steroidal anti-inflammatory drugs (indomethacin) and coxibs (celecoxib) which are used clinically in the treatment of inflammatory pain.

Experiments were in male Wistar rats weighing (141-175 g). In brief, the rats' paw withdrawal threshold (PWT) to a mechanical compression of the hind paw was measured (baseline reading) using a Randall-Sellito apparatus (Ugo Basile). A cut-off of 20 g was employed to minimise tissue damage to the paw. The animals were then lightly anaesthetised with isoflurane (1-3%) and CFA (0.1 ml.paw$^{-1}$) injected subcutaneously (s.c.) into the plantar surface of the left hind paw. The animals were then returned to their home cage and left for the inflammation to develop.

Twenty four h after CFA injection, PWT's were re-measured (0 min) and immediately after this reading, rats were dosed orally with either vehicle or compound 3K (4.5-45 µmol/kg p.o.) Readings were then made at 3 h post drug administration.

Data were plotted as mean±s.e.m. and compared between groups using the Kruskal-Wallis one-way analysis of variance, a non-parametric statistical test. If statistical significance (P<0.05) was observed with this test, the vehicle group and each of the treatment groups were compared using the non-parametric Dunn's test.

The percent attenuation of mechanical hyperalgesia is calculated as follows.

$$\% \text{ attenuation of hyperalgesia} = \frac{\left(\begin{array}{c}\text{Post compound } PWT - \\ \text{post } CFA \ PWT\end{array}\right)}{\left(\begin{array}{c}\text{Baseline } PWT - \\ \text{post } CFA \ PWT\end{array}\right)} \times 100$$

Oral administration of compound 3K (4.5-45 µmol/kg) reversed mechanical hyperalgesia induced by CFA in a dose-dependent fashion (Table 2). The MED for 3K was 4.4 µmol/kg p.o. These data demonstrate that the selective CB2 receptor agonists possess potent oral anti-algesic activity in a rat model of inflammatory pain.

TABLE 2

Effect of compound 3K on mechanical hyperalgesia induced by complete Freund's adjuvant administered 24 h previously in rats.

| Compound | Route | Dose (µmol/kg) | Number of animals tested | % Attenuation of hyperalgesia (peak effect) |
|---|---|---|---|---|
| Vehicle | p.o. | 2 ml·kg$^{-1}$ | 7 | −0.6 ± 11 |
| 3K | p.o. | 4.5 | 7 | 36 ± 11 |
| 3K | p.o. | 45 | 8 | 100 ± 25** |

Dose groups and number of animals per group.
*p ≤ 0.01
**p ≤ 0.001, Dunns test comparing vehicle-treated and compound-treated animals.

The invention claimed is:

1. A 1-(biphenyl-4-ylmethyl)imidazolidine-2,4-dione derivative the general Formula I represented by

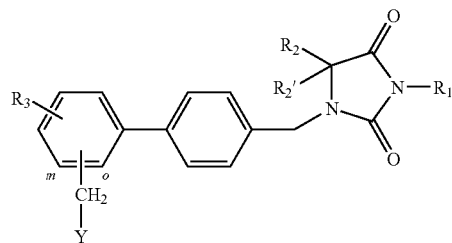

Formula I wherein
R$_1$ is 1) H, 2) (C$_{1-6}$)alkyl wherein the alkyl is optionally substituted with oxo, OR$_4$, COOR$_5$, halogen or CN, 3) (C$_{2-6}$)alkenyl, 4) (C$_{2-6}$)alkynyl, 5) (C$_{3-6}$)cycloalkyl or 6) (C$_{3-6}$)cycloalkyl(C$_{1-3}$)alkyl;
R$_2$ and R$_2$' are independently H or (C$_{1-3}$)alkyl; or
R$_2$ and R$_2$' form together with the carbon atom to which they are bound a (C$_{3-5}$)-cycloalkyl group;
R$_3$ represents H or 1 to 4 F substituents;
Y represents

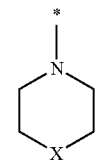

or NR$_8$R$_9$;
X represents CHR$_6$, CF$_2$, O, S, SO or SO$_2$;
R$_4$ and R$_5$ are (C$_{1-6}$)alkyl;
R$_6$ is H, OR$_7$ or CN;
R$_7$ is (C$_{1-3}$)alkyl;
R$_8$ is (C$_{5-7}$)cycloalkyl comprising a heteroatom selected from O, S, SO and SO$_2$;
R$_9$ is H or (C$_{1-4}$)alkyl;
o and m represent the ortho or meta position of the substituent Y—CH$_2$;
or a pharmaceutically acceptable salt thereof.

2. The 1-(biphenyl-4-ylmethyl)imidazolidine-2,4-dione derivative of claim 1, wherein R$_3$ represent a para-fluoro substituent.

3. The 1-(biphenyl-4-ylmethyl)imidazolidine-2,4-dione derivative of claim 1, wherein Y—CH$_2$ is a meta substituent and wherein Y represents NR$_8$R$_9$ and R$_8$ is tetrahydropyran-4-yl or tetrahydrofuran-3-yl.

4. The 1-(biphenyl-4-ylmethyl)imidazolidine-2,4-dione derivative of claim 1, wherein Y represents

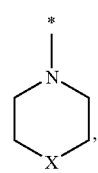

and wherein

R₁ is 1) H, 2) (C₁₋₆)alkyl wherein the alkyl is optionally substituted with oxo, OR₄, COOR₅, halogen or CN, 3) (C₂₋₆)alkenyl, 4) (C₂₋₆)alkynyl, 5) (C₃₋₆)cycloalkyl or 6) (C₃₋₆)cycloalkyl(C₁₋₃)alkyl;

R₂ and R₂' are independently H or (C₁₋₃)alkyl; or

R₂ and R₂' form together with the carbon atom to which they are bound a (C₃₋₅)-cycloalkyl group;

R₃ represents H or 1 to 4 F substituents;

X represents CHR₆, CF₂, O, S, SO or SO₂;

R₄ and R₅ are (C₁₋₆)alkyl;

R₆ is H, OR₇ or CN;

R₇ is (C₁₋₃)alkyl;

o and m represent the ortho or meta position of the aminomethylene substituent;

or a pharmaceutically acceptable salt thereof.

5. The 1-(biphenyl-4-ylmethyl)imidazolidine-2,4-dione derivative of claim 4, wherein X is CH₂, CF₂ or O.

6. The 1-(biphenyl-4-ylmethyl)imidazolidine-2,4-dione derivative of claim 5, wherein R₁ is 1) (C₁₋₆)alkyl wherein the alkyl is optionally substituted with F, 2) (C₃₋₆)cycloalkyl or 3) (C₃₋₆)cycloalkyl-(C₁₋₃)alkyl and R₂ and R₂' are H.

7. The 1-(biphenyl-4-ylmethyl)imidazolidine-2,4-dione derivative of claim 1 which is selected from 1-(2'-(morpholin-4-ylmethyl)biphenyl-4-ylmethyl)-3-propyl-imidazolidine-2,4-dione;

3-isobutyl-1-(2'-(morpholin-4-ylmethyl)biphenyl-4-ylmethyl)imidazolidine-2,4-dione;

3-butyl-1-(2'-(morpholin-4-ylmethyl)biphenyl-4-ylmethyl)imidazolidine-2,4-dione;

3-cyclobutylmethyl-1-(2'-(morpholin-4-ylmethyl)biphenyl-4-ylmethyl)imidazolidine-2,4-dione;

3-allyl-1-(2'-(morpholin-4-ylmethyl)biphenyl-4-ylmethyl)imidazolidine-2,4-dione;

1-(2'-(morpholin-4-ylmethyl)biphenyl-4-ylmethyl)-3-prop-2-ynyl-imidazolidine-2,4-dione;

3-(2,2-difluoro-ethyl)-1-(2'-(morpholin-4-ylmethyl)biphenyl-4-ylmethyl)imidazolidine-2,4-dione;

3-(2-fluoro-ethyl)-1-(2'-(morpholin-4-ylmethyl)biphenyl-4-ylmethyl)imidazolidine-2,4-dione;

3-(2-methoxy-ethyl)-1-(2'-(morpholin-4-ylmethyl)biphenyl-4-ylmethyl)imidazolidine-2,4-dione;

3-((2'-(morpholin-4-ylmethyl)biphenyl-4-ylmethyl)-2,5-dioxo-imidazolidin-1-yl)-acetic acid methyl ester;

1-(2'-(morpholin-4-ylmethyl)biphenyl-4-ylmethyl)-3-(2-oxo-butyl)imidazolidine-2,4-dione;

3-cyclopropylmethyl-1-(2'-(morpholin-4-ylmethyl)biphenyl-4-ylmethyl)imidazolidine-2,4-dione;

1-(3'-(4,4-difluoro-piperidin-1-ylmethyl)biphenyl-4-ylmethyl)imidazolidine-2,4-dione;

3-allyl-1-(3'-(4,4-difluoro-piperidin-1-ylmethyl)biphenyl-4-ylmethyl)imidazolidine-2,4-dione;

3-cyclobutylmethyl-1-(3'-(4,4-difluoro-piperidin-1-ylmethyl)biphenyl-4-ylmethyl)imidazolidine-2,4-dione;

3-cyclopropyl-1-(4'-fluoro-3'-(morpholin-4-ylmethyl)biphenyl-4-ylmethyl)imidazolidine-2,4-dione;

1-(4'-(3-cyclopropylmethyl-2,4-dioxo-imidazolidin-1-ylmethyl)biphenyl-2-yl-methyl)-piperidine-4-carbonitrile;

3-cyclopropylmethyl-1-(2'-(piperidin-1-ylmethyl)biphenyl-4-ylmethyl)imidazolidine-2,4-dione;

3-cyclopropyl-1-(3'-(thiomorpholin-4-ylmethyl)biphenyl-4-ylmethyl)imidazolidine-2,4-dione;

3-cyclopropyl-1-(3'-(1,1-dioxo-1λ⁶-thiomorpholin-4-ylmethyl)biphenyl-4-ylmethyl)imidazolidine-2,4-dione;

3-isobutyl-1-(3'-(piperidin-1-ylmethyl)biphenyl-4-ylmethyl)imidazolidine-2,4-dione;

1-(4'-fluoro-3'-(morpholin-4-ylmethyl)biphenyl-4-ylmethyl)-3-isobutyl-imidazolidine-2,4-dione;

1-(2'-fluoro-5'-(morpholin-4-ylmethyl)biphenyl-4-ylmethyl)-3-isobutyl-imidazolidine-2,4-dione;

1-(2'-fluoro-3'-(morpholin-4-ylmethyl)biphenyl-4-ylmethyl)-3-isobutyl-imidazolidine-2,4-dione;

3-cyclobutylmethyl-1-(3'-(piperidin-1-ylmethyl)biphenyl-4-ylmethyl)imidazolidine-2,4-dione;

3-(2,2-difluoro-ethyl)-1-(3'-(piperidin-1-ylmethyl)biphenyl-4-ylmethyl)-imidazolidine-2,4-dione;

1-(4'-fluoro-3'-(piperidin-1-ylmethyl)biphenyl-4-ylmethyl)-3-isobutyl-imidazolidine-2,4-dione;

3-(2,2-difluoro-ethyl)-1-(2'-fluoro-3'-(piperidin-1-ylmethyl)biphenyl-4-ylmethyl)-imidazolidine-2,4-dione;

1-(2'-fluoro-3'-(piperidin-1-ylmethyl)biphenyl-4-ylmethyl)-3-isobutyl-imidazolidine-2,4-dione;

1-(3'-fluoro-5'-(piperidin-1-ylmethyl)biphenyl-4-ylmethyl)-3-isobutyl-imidazolidine-2,4-dione;

1-(3'-(1,1-dioxo-1λ⁶-thiomorpholin-4-ylmethyl)-4'-fluoro-biphenyl-4-ylmethyl)-3-isobutyl-imidazolidine-2,4-dione;

3-cyclopropylmethyl-1-(3'-(1,1-dioxo-1λ⁶-thiomorpholin-4-ylmethyl)biphenyl-4-ylmethyl)imidazolidine-2,4-dione;

3-cyclopropylmethyl-1-(3'-(1,1-dioxo-1λ⁶-thiomorpholin-4-ylmethyl)-4'-fluoro-biphenyl-4-ylmethyl)imidazolidine-2,4-dione;

1-(3'-(1,1-dioxo-1λ⁶-thiomorpholin-4-ylmethyl)biphenyl-4-ylmethyl)-3-isobutyl-imidazolidine-2,4-dione;

3-cyclobutyl-1-((4'-fluoro-3'-(thiomorpholinomethyl)biphenyl-4-yl)methyl)imidazolidine-2,4-dione;

3-cyclobutyl-1-(3'-(1,1-dioxo-1λ⁶-thiomorpholin-4-ylmethyl)biphenyl-4-ylmethyl)imidazolidine-2,4-dione;

3-cyclobutyl-1-(3'-(1,1-dioxo-1λ⁶-thiomorpholin-4-ylmethyl)-4'-fluoro-biphenyl-4-ylmethyl)imidazolidine-2,4-dione;

3-cyclopropyl-1-(3'-(1,1-dioxo-1λ⁶-thiomorpholin-4-ylmethyl)biphenyl-4-ylmethyl)imidazolidine-2,4-dione;

(S)-3-(cyclopropylmethyl)-1-((4'-fluoro-3'-((tetrahydrofuran-3-ylamino)methyl)-biphenyl-4-yl)methyl)imidazolidine-2,4-dione;

(R)-3-(cyclopropylmethyl)-1-((4'-fluoro-3'-((tetrahydrofuran-3-ylamino)methyl)biphenyl-4-yl)methyl)imidazolidine-2,4-dione;

3-(cyclopropylmethyl)-1-((4'-fluoro-3'-((tetrahydro-2H-pyran-4-ylamino)methyl)biphenyl-4-yl)methyl)imidazolidine-2,4-dione;

1-((3'-((tetrahydro-2H-pyran-4-ylamino)methyl)biphenyl-4-yl)methyl)-3-(2,2,2-trifluoroethyl)imidazolidine-2,4-dione;

(R)-1-((4'-fluoro-3'-((tetrahydrofuran-3-ylamino)methyl)biphenyl-4-yl)methyl)-3-(2,2,2-trifluoroethyl)imidazolidine-2,4-dione;

(S)-1-((4'-fluoro-3'-((tetrahydrofuran-3-ylamino)methyl)biphenyl-4-yl)methyl)-3-(2,2,2-trifluoroethyl)imidazolidine-2,4-dione;

(R)-1-((4'-fluoro-3'-((tetrahydrofuran-3-ylamino)methyl)biphenyl-4-yl)methyl)-3-isopropylimidazolidine-2,4-dione;

1-((4'-fluoro-3'-((tetrahydro-2H-pyran-4-ylamino)methyl)biphenyl-4-yl)methyl)-3-isopropylimidazolidine-2,4-dione;

(S)-1-((4'-fluoro-3'-((tetrahydrofuran-3-ylamino)methyl)biphenyl-4-yl)methyl)-3-isopropylimidazolidine-2,4-dione; and 1-((4'-fluoro-3'-((tetrahydro-2H-pyran-4-ylamino)methyl)biphenyl-4-yl)methyl)-3-(2,2,2-trifluoroethyl)imidazolidine-2,4-dione or a pharmaceutically acceptable salt thereof.

8. A pharmaceutical composition comprising a 1-(biphenyl-4-ylmethyl)imidazolidine-2,4-dione derivative of claim 1 or a pharmaceutically acceptable salt thereof in admixture with one or more pharmaceutically acceptable auxiliaries.

9. A pharmaceutical composition comprising a 1-(biphenyl-4-ylmethyl)imidazolidine-2,4-dione derivative of claim 7 or a pharmaceutically acceptable salt thereof in admixture with one or more pharmaceutically acceptable auxiliaries.

10. A method of treatment of pain comprising administering to a patient in need thereof a therapeutically effective amount of a 1-(biphenyl-4-ylmethyl)imidazolidine-2,4-dione derivative of claim 1 or a pharmaceutically acceptable salt thereof.

11. The method of claim 10, wherein the pain is selected from the group consisting of peri-operative pain, chronic pain, neuropathic pain, and pain and spasticity associated with multiple sclerosis.

12. A method of treatment of pain comprising administering to a patient in need thereof a therapeutically effective amount of a 1-(biphenyl-4-ylmethyl)imidazolidine-2,4-dione derivative of claim 7 or a pharmaceutically acceptable salt thereof.

13. The method of claim 12, wherein the pain is selected from the group consisting of peri-operative pain, chronic pain, neuropathic pain, and pain and spasticity associated with multiple sclerosis.

* * * * *